US010061058B2

(12) United States Patent
Cortelyou et al.

(10) Patent No.: US 10,061,058 B2
(45) Date of Patent: Aug. 28, 2018

(54) TRACKING SYSTEM AND METHOD FOR USE IN SURVEYING AMUSEMENT PARK EQUIPMENT

(71) Applicant: Universal City Studios LLC, Universal City, CA (US)

(72) Inventors: Robert J. Cortelyou, Orlando, FL (US); Steven C. Blum, Orlando, FL (US); Paula Stenzler, Orlando, FL (US); Christopher Oliver, Orlando, FL (US); Brian B. McQuillian, Orlando, FL (US); Justin M. Schwartz, Orlando, FL (US); Michael R. Kiddoo, Orlando, FL (US)

(73) Assignee: Universal City Studios LLC, Universal City, CA (US)

( * ) Notice: Subject to any disclaimer, the term of this patent is extended or adjusted under 35 U.S.C. 154(b) by 182 days.

(21) Appl. No.: 14/717,921

(22) Filed: May 20, 2015

(65) Prior Publication Data
US 2015/0338548 A1 Nov. 26, 2015

Related U.S. Application Data

(60) Provisional application No. 62/001,551, filed on May 21, 2014.

(51) Int. Cl.
*G01V 8/14* (2006.01)
*G01N 21/84* (2006.01)
(Continued)

(52) U.S. Cl.
CPC ............. *G01V 8/14* (2013.01); *G01N 17/008* (2013.01); *G01N 21/8422* (2013.01);
(Continued)

(58) Field of Classification Search
CPC ......... G01N 17/008; G01N 2021/8896; G01N 21/8422; G01N 21/8851; G01V 8/14;
(Continued)

(56) References Cited

U.S. PATENT DOCUMENTS 2,170,160 A 8/1939 Bailey
3,740,562 A 6/1973 Fertig
(Continued)

FOREIGN PATENT DOCUMENTS

CN 201189396 2/2009
EP 1578130 9/2005
(Continued)

OTHER PUBLICATIONS

Chen, X.; "Capturing Fast Motion with Consumer Grade Unsynchronized Rolling-Shutter Cameras"; The University of British Columbia 2012, pp. 1-85.
(Continued)

*Primary Examiner* — Thanh Luu
(74) *Attorney, Agent, or Firm* — Fletcher Yoder, P.C.

(57) ABSTRACT

A dynamic signal to noise ratio tracking system enables detection and tracking of amusement park equipment within the field of view of the tracking system. The tracking system may include an emitter configured to emit electromagnetic radiation within an area, a detector configured to detect electromagnetic radiation reflected back from vehicles within the area, and a control unit configured to evaluate signals from the detector to survey the amusement park equipment to determine whether the equipment has degraded or shifted.

20 Claims, 15 Drawing Sheets

(51) Int. Cl.
  *G01N 21/88* (2006.01)
  *G01N 17/00* (2006.01)
  *G06K 9/00* (2006.01)
  *G06T 7/20* (2017.01)

(52) U.S. Cl.
  CPC ..... *G01N 21/8851* (2013.01); *G06K 9/00771* (2013.01); *G06T 7/20* (2013.01); *G01N 2021/8896* (2013.01); *G06T 2207/10048* (2013.01); *G06T 2207/30196* (2013.01); *G06T 2207/30204* (2013.01); *G06T 2207/30208* (2013.01); *G06T 2207/30232* (2013.01)

(58) Field of Classification Search
  CPC ...... G06K 9/00771; G06T 2207/10048; G06T 2207/30196; G06T 2207/30204; G06T 2207/30208; G06T 2207/30232; G06T 7/20; G01B 11/03; G01B 11/16; G01C 15/002; G01C 3/00; E04B 1/00
  See application file for complete search history.

(56) References Cited

U.S. PATENT DOCUMENTS

| | | | |
|---|---|---|---|
| 3,743,217 A | 7/1973 | Turck | |
| 4,254,433 A | 3/1981 | Dewar, Jr. et al. | |
| 4,662,756 A | 5/1987 | Duran, Jr. | |
| 4,855,915 A | 8/1989 | Dallaire | |
| 5,210,604 A | 5/1993 | Carpenter | |
| 5,365,266 A | 11/1994 | Carpenter | |
| 5,682,331 A | 10/1997 | Berlin | |
| 5,809,161 A | 9/1998 | Auty et al. | |
| 6,008,800 A | 12/1999 | Pryor | |
| 6,176,837 B1 | 1/2001 | Foxlin | |
| 6,342,706 B1 | 1/2002 | Takeda | |
| 6,474,159 B1 | 11/2002 | Foxlin et al. | |
| 6,665,079 B1 | 12/2003 | Tocci et al. | |
| 6,711,280 B2 | 3/2004 | Stafsudd | |
| 6,720,949 B1 | 4/2004 | Pryor et al. | |
| 6,761,637 B2 | 7/2004 | Weston et al. | |
| 6,784,826 B2 | 8/2004 | Kane et al. | |
| 6,831,603 B2 | 12/2004 | Menache | |
| 6,950,021 B2 | 9/2005 | Butler | |
| 6,967,566 B2 | 11/2005 | Weston et al. | |
| 7,084,859 B1 | 8/2006 | Pryor | |
| 7,089,148 B1 | 8/2006 | Bachmann et al. | |
| 7,098,891 B1 | 8/2006 | Pryor | |
| 7,184,022 B2 | 2/2007 | Xie et al. | |
| 7,257,237 B1 | 8/2007 | Luck et al. | |
| 7,259,747 B2 | 8/2007 | Bell | |
| 7,307,617 B2 | 12/2007 | Wilson et al. | |
| 7,356,172 B2 | 4/2008 | Fan et al. | |
| 7,395,181 B2 | 7/2008 | Foxlin | |
| 7,401,783 B2 | 7/2008 | Pryor | |
| 7,445,550 B2 | 11/2008 | Barney et al. | |
| 7,466,843 B2 | 12/2008 | Pryor | |
| 7,489,303 B1 | 2/2009 | Pryor | |
| 7,500,917 B2 | 3/2009 | Barney et al. | |
| 7,502,126 B2 | 3/2009 | Ong | |
| 7,505,033 B2 | 3/2009 | Guo et al. | |
| 7,519,537 B2 | 4/2009 | Rosenberg | |
| 7,618,323 B2 | 11/2009 | Rothschild et al. | |
| 7,623,115 B2 | 11/2009 | Marks | |
| 7,671,851 B1 | 3/2010 | Pryor | |
| 7,704,135 B2 | 4/2010 | Harrison, Jr. | |
| 7,755,608 B2 | 7/2010 | Chang et al. | |
| 7,775,439 B2 | 8/2010 | Kimber et al. | |
| 7,775,883 B2 | 8/2010 | Smoot et al. | |
| 7,843,429 B2 | 11/2010 | Pryor | |
| 7,850,527 B2 | 12/2010 | Barney et al. | |
| 7,854,655 B2 | 12/2010 | Mao et al. | |
| 7,863,551 B2 | 1/2011 | Bang et al. | |
| 7,874,918 B2 | 1/2011 | Osnato et al. | |
| 7,896,742 B2 | 3/2011 | Weston et al. | |
| 7,905,769 B1 | 3/2011 | Harrison, Jr. | |
| 7,918,733 B2 | 4/2011 | Zalewski et al. | |
| 7,927,216 B2 | 4/2011 | Ikeda et al. | |
| 7,996,793 B2 | 8/2011 | Latta et al. | |
| 8,040,328 B2 | 10/2011 | Smith et al. | |
| 8,058,975 B2 | 11/2011 | Barnardo et al. | |
| 8,209,134 B2 | 6/2012 | Parker et al. | |
| 8,228,305 B2 | 7/2012 | Pryor | |
| 8,248,367 B1 | 8/2012 | Barney et al. | |
| 8,287,374 B2 | 10/2012 | Pryor | |
| 8,306,635 B2 | 11/2012 | Pryor | |
| 8,538,562 B2 | 9/2013 | Pryor et al. | |
| 8,553,079 B2 | 10/2013 | Pryor | |
| 9,316,593 B2 | 4/2016 | Switkes | |
| 9,513,606 B1 | 12/2016 | Larsen | |
| 9,649,551 B2 | 5/2017 | Maharbiz | |
| 2003/0048926 A1 | 3/2003 | Watanabe | |
| 2003/0069077 A1 | 4/2003 | Koreienek et al. | |
| 2004/0102247 A1 | 5/2004 | Smoot et al. | |
| 2004/0166937 A1 | 8/2004 | Kopera et al. | |
| 2004/0178955 A1 | 9/2004 | Menache et al. | |
| 2005/0128578 A1 | 6/2005 | Sugawara | |
| 2005/0143173 A1 | 6/2005 | Barney et al. | |
| 2006/0030385 A1 | 2/2006 | Barney et al. | |
| 2006/0125691 A1 | 6/2006 | Menache et al. | |
| 2006/0154726 A1 | 7/2006 | Weston et al. | |
| 2006/0256081 A1 | 11/2006 | Zalewski et al. | |
| 2006/0282873 A1 | 12/2006 | Zalewski et al. | |
| 2006/0287087 A1 | 12/2006 | Zalewski et al. | |
| 2007/0259594 A1 | 11/2007 | Galbiati et al. | |
| 2007/0265075 A1 | 11/2007 | Zalewski | |
| 2008/0013826 A1 | 1/2008 | Hillis et al. | |
| 2008/0014835 A1 | 1/2008 | Weston et al. | |
| 2008/0074652 A1 | 3/2008 | Fouquet | |
| 2008/0096654 A1 | 4/2008 | Mondesir et al. | |
| 2008/0125896 A1 | 5/2008 | Troy et al. | |
| 2008/0158555 A1 | 7/2008 | Mori | |
| 2008/0244468 A1 | 10/2008 | Nishihara et al. | |
| 2009/0051653 A1 | 2/2009 | Barney et al. | |
| 2009/0066784 A1 | 3/2009 | Stone et al. | |
| 2009/0115721 A1 | 5/2009 | Aull et al. | |
| 2009/0121894 A1 | 5/2009 | Wilson et al. | |
| 2009/0124165 A1 | 5/2009 | Weston | |
| 2009/0191968 A1 | 7/2009 | Johnson et al. | |
| 2009/0215534 A1 | 8/2009 | Wilson et al. | |
| 2009/0222149 A1 | 9/2009 | Murray et al. | |
| 2009/0278915 A1 | 11/2009 | Kramer et al. | |
| 2009/0303069 A1 | 12/2009 | Carl, Jr. | |
| 2009/0316952 A1 | 12/2009 | Ferren et al. | |
| 2010/0040292 A1 | 2/2010 | Clarkson | |
| 2010/0050133 A1 | 2/2010 | Nishihara et al. | |
| 2010/0128259 A1* | 5/2010 | Bridges | G01B 11/03 356/138 |
| 2010/0133424 A1 | 6/2010 | Lindsay | |
| 2010/0134308 A1 | 6/2010 | Barnardo et al. | |
| 2010/0292007 A1 | 7/2010 | Tarra et al. | |
| 2010/0194762 A1 | 8/2010 | Latta et al. | |
| 2010/0199228 A1 | 8/2010 | Latta et al. | |
| 2010/0199230 A1 | 8/2010 | Latta et al. | |
| 2010/0208129 A1 | 8/2010 | Rindfuss et al. | |
| 2010/0215215 A1 | 8/2010 | Ueshima | |
| 2010/0281436 A1 | 11/2010 | Kipman et al. | |
| 2010/0304868 A1 | 12/2010 | Zalewski | |
| 2010/0306712 A1 | 12/2010 | Snook et al. | |
| 2010/0306714 A1 | 12/2010 | Latta et al. | |
| 2010/0306715 A1 | 12/2010 | Geisner et al. | |
| 2010/0306716 A1 | 12/2010 | Perez | |
| 2011/0081970 A1 | 4/2011 | Barney et al. | |
| 2011/0093219 A1* | 4/2011 | Parker | G01B 11/03 702/34 |
| 2011/0118021 A1 | 5/2011 | Zalewski | |
| 2011/0151974 A1 | 6/2011 | Deaguero | |
| 2011/0174189 A1 | 7/2011 | Beutler | |
| 2011/0183751 A1 | 7/2011 | Ueshima | |
| 2011/0301757 A1 | 12/2011 | Jones | |
| 2012/0218107 A1 | 8/2012 | Mimeault | |
| 2012/0262366 A1 | 10/2012 | Zhu et al. | |
| 2013/0177296 A1 | 7/2013 | Geisner et al. | |
| 2013/0188839 A1 | 7/2013 | Abraham et al. | |
| 2013/0300637 A1 | 11/2013 | Smits | |

(56) References Cited

U.S. PATENT DOCUMENTS

| | | |
|---|---|---|
| 2013/0320236 A1 | 12/2013 | Ohta |
| 2013/0342813 A1 | 12/2013 | Wang |
| 2014/0036076 A1 | 2/2014 | Nerayoff et al. |
| 2014/0166854 A1 | 6/2014 | Kowalevicz |
| 2014/0240102 A1 | 8/2014 | Kawash et al. |
| 2014/0314278 A1 | 10/2014 | Tatsuzawa et al. |

FOREIGN PATENT DOCUMENTS

| | | | |
|---|---|---|---|
| JP | H11211831 A | | 8/1999 |
| JP | 2012120648 | | 6/2012 |
| JP | 2012226666 A | | 11/2012 |
| JP | 2013175221 A | | 9/2013 |
| WO | 9515505 A1 | | 6/1995 |

OTHER PUBLICATIONS

Chung, J. et al.; "Vision Based Motion Tracking System for Interactive Entertainment Applications"; ETRI 2005, pp. 1-6.

Hargather, M. et al.; "Retroreflective Shadowgraph Technique for Large-Scale Flow Visualization"; Applied Optics vol. 48(22) 2009, pp. 4449-4457.

Sparacino, F. et al.; "Media in Performance: Interactive Spaces for Dance, Theater, Circus, and Museum Exhibits"; IBM Systems Journal vol. 39 (3&4) 2000, pp. 479-510.

PCT/US2015/032051 International Search Report and Written Opinion dated Sep. 8, 2015.

Ouchi et al., "Magic Wand: An Intuitive Gesture Remote Control for Home Appliances," May 2005.

3M, "Retroreflection," Personal Safety Products, 3M Occupational health and Environmental Safety Division; St. Paul, Minnesota, 2005, www.3M.com/Scotchlite.

"Basic Surveying—Theory and Practice," Oregon Department of Transportation Geometrics Unit, Feb. 15-17, 2000, Bend, Oregon.

Andrew Gastineau et al: "Bridge Health Monitoring and Inspections Systems—A Survey of Methods", XP055400986, Retrieved from the Internet: URL:http://conservancy.umn.edu/bitstream/handle/11299/150962/Mn_DOT2009-29.pdf?sequence=1&isAllowed=y [retrieved on Aug. 24, 2017], Sep. 1, 2009.

* cited by examiner

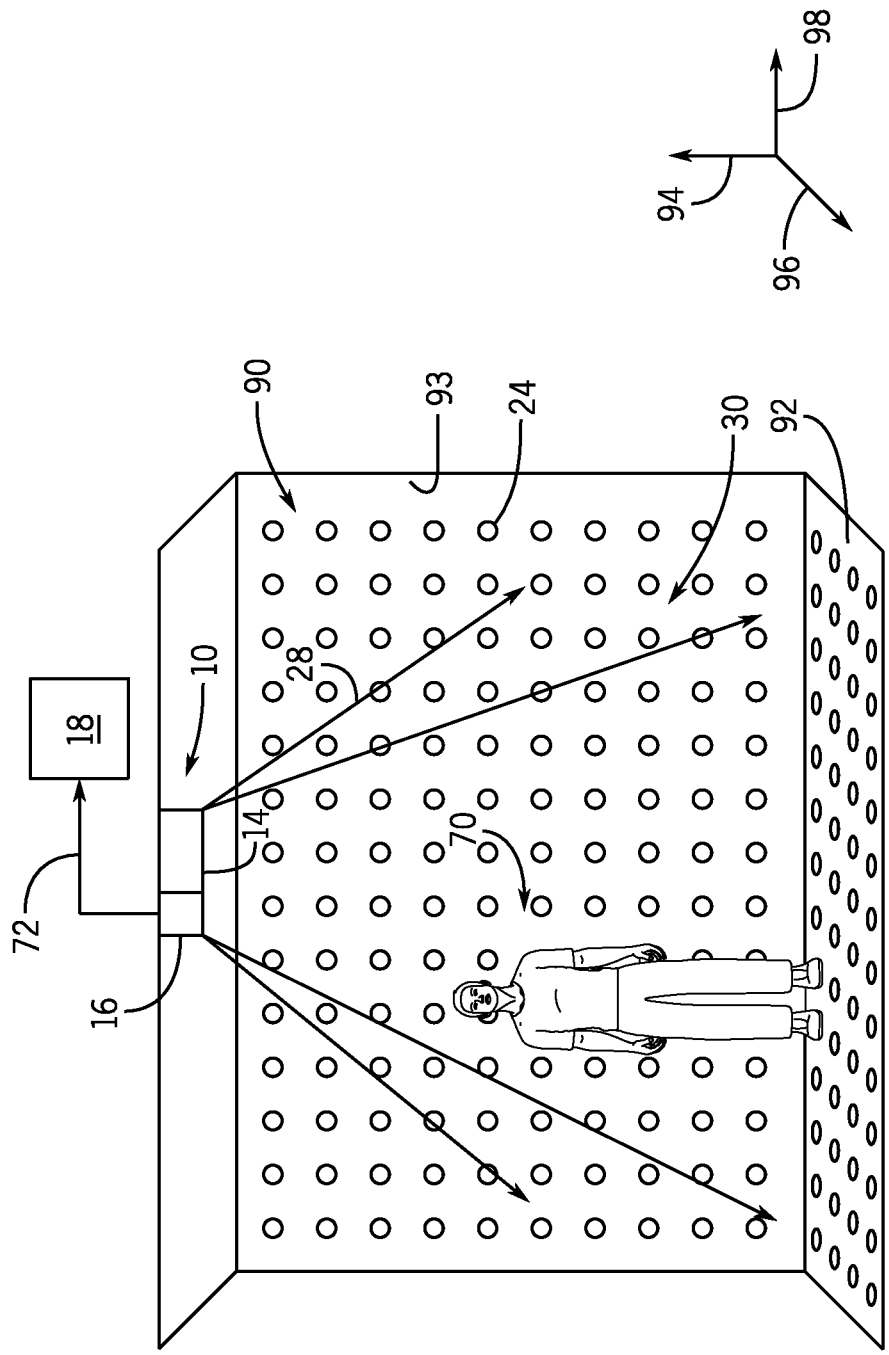

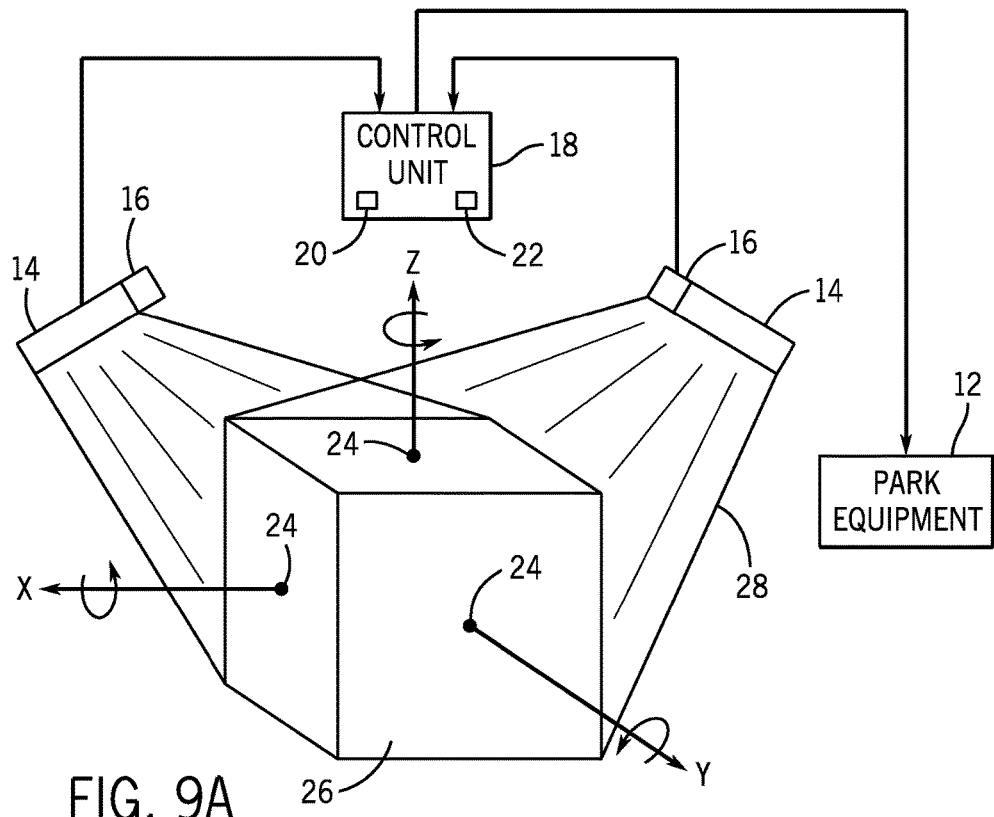
FIG. 9A
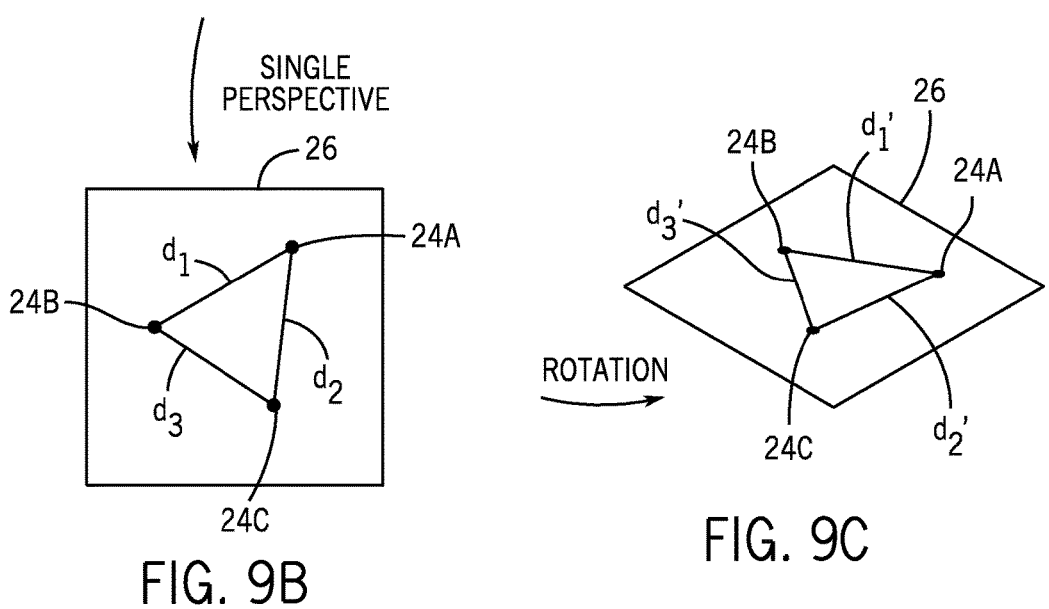
FIG. 9B
FIG. 9C

TRACKING SYSTEM AND METHOD FOR USE IN SURVEYING AMUSEMENT PARK EQUIPMENT

CROSS REFERENCE TO RELATED APPLICATIONS

This application claims the benefit of U.S. Provisional Application No. 62/001,551, filed May 21, 2014, which is incorporated herein by reference in its entirety for all purposes.

BACKGROUND

The present disclosure relates generally to the field of tracking systems and, more particularly, to methods and equipment used to enable tracking of elements in a variety of contexts through a dynamic signal to noise ratio tracking system.

Tracking systems have been widely used to track motion, position, orientation, and distance, among other aspects, of objects in a wide variety of contexts. Such existing tracking systems generally include an emitter that emits electromagnetic energy and a detector configured to detect the electromagnetic energy, sometimes after it has been reflected off an object. It is now recognized that traditional tracking systems have certain disadvantages and that improved tracking systems are desired for use in a variety of contexts, including amusement park attractions, workplace monitoring, sports, fireworks displays, factory floor management, robotics, security systems, parking, and transportation, among others.

BRIEF DESCRIPTION

In accordance with an embodiment of the present disclosure, an amusement park surveying system includes an amusement park feature having a retro-reflective marker; an emitter configured to emit electromagnetic radiation toward the retro-reflective marker; a detector configured to detect retro-reflection of the electromagnetic radiation from the retro-reflective marker while filtering electromagnetic radiation that is not retro-reflected; and a control system communicatively coupled to the detector and comprising processing circuitry configured to: monitor the retro-reflected electromagnetic radiation from the retro-reflective marker against a reference signature of retro-reflected electromagnetic radiation from the retro-reflective marker stored in memory; and identify differences between the electromagnetic radiation retro-reflected by the retro-reflective marker and the reference signature of retro-reflected electromagnetic radiation to evaluate a condition of the amusement park feature.

In accordance with another embodiment of the present disclosure, a method of surveying amusement park features includes directing electromagnetic radiation toward an amusement park feature positioned within an amusement park attraction area using an emitter, the amusement park feature having a retro-reflective marker; detecting electromagnetic radiation retro-reflected from the retro-reflective marker disposed on the amusement park feature while filtering out electromagnetic radiation that is not retro-reflected using a detector; monitoring the retro-reflected electromagnetic radiation from the retro-reflective marker against a reference signature of retro-reflected electromagnetic radiation from the retro-reflective marker stored in memory using processing circuitry of a control system in communication with the detector; and identifying differences between the electromagnetic radiation retro-reflected by the retro-reflective marker and the reference signature of retro-reflected electromagnetic radiation to evaluate a condition of the amusement park feature.

In accordance with a further embodiment of the present disclosure, a survey system configured to survey amusement park features includes a retro-reflective marker; an emitter configured to emit electromagnetic radiation toward the retro-reflective marker; a detector correlated to electromagnetic radiation retro-reflected by the retro-reflective marker and configured to detect retro-reflection of the electromagnetic radiation from the retro-reflective marker while filtering electromagnetic radiation that is not retro-reflected; and a control system communicatively coupled to the emitter and the detector and having processing circuitry configured to: monitor the retro-reflected electromagnetic radiation from the retro-reflective marker against a reference signature of retro-reflected electromagnetic radiation from the retro-reflective marker stored in memory; and identify differences between the electromagnetic radiation retro-reflected by the retro-reflective marker and the reference signature of retro-reflected electromagnetic radiation, including differences in position or orientation, to evaluate a condition of an amusement park feature; and wherein the emitter, the detector, and at least a portion of the processing circuitry of the control system are integrated with or form a part of surveying equipment, the surveying equipment comprising a total station, a robotic total station, an electronic distance meter, a theodolite, or any combination thereof.

DRAWINGS

These and other features, aspects, and advantages of the present disclosure will become better understood when the following detailed description is read with reference to the accompanying drawings in which like characters represent like parts throughout the drawings, wherein:

FIG. 7 is an elevational view of a room with a grid pattern of retro-reflective markers disposed on a wall and a floor of the room for tracking a position of people and objects in the room via the tracking system of FIG. 1, in accordance with an embodiment of the present disclosure;

FIGS. 9A-9C depict the manner in which an object may be tracked in three spatial dimensions by the tracking system of FIG. 1, in accordance with an embodiment of the present disclosure;

Figure 1:
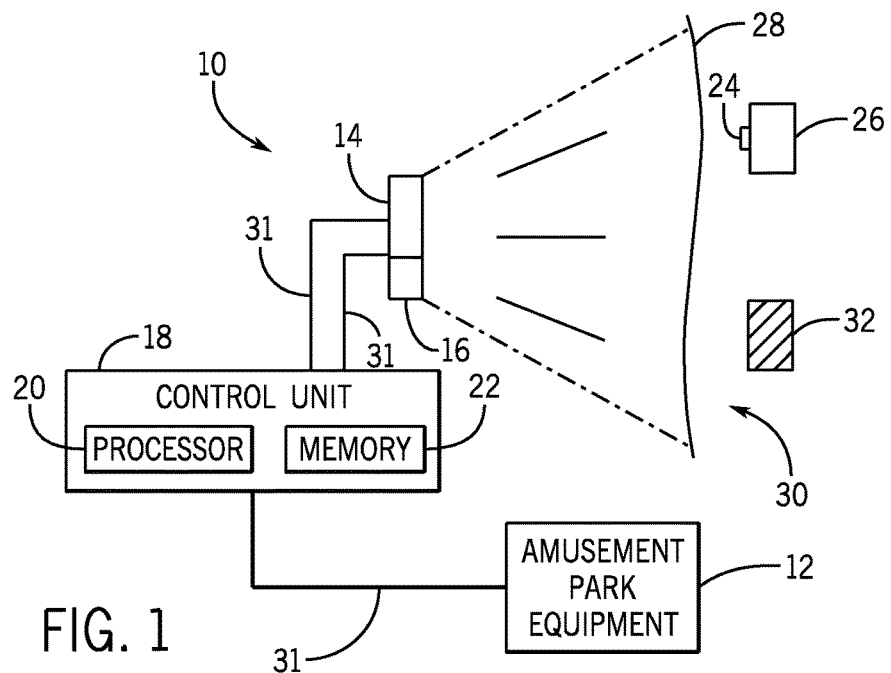
FIG. 1 is a schematic diagram of a tracking system utilizing a dynamic signal to noise ratio device to track objects, in accordance with an embodiment of the present disclosure.
Figure 17:
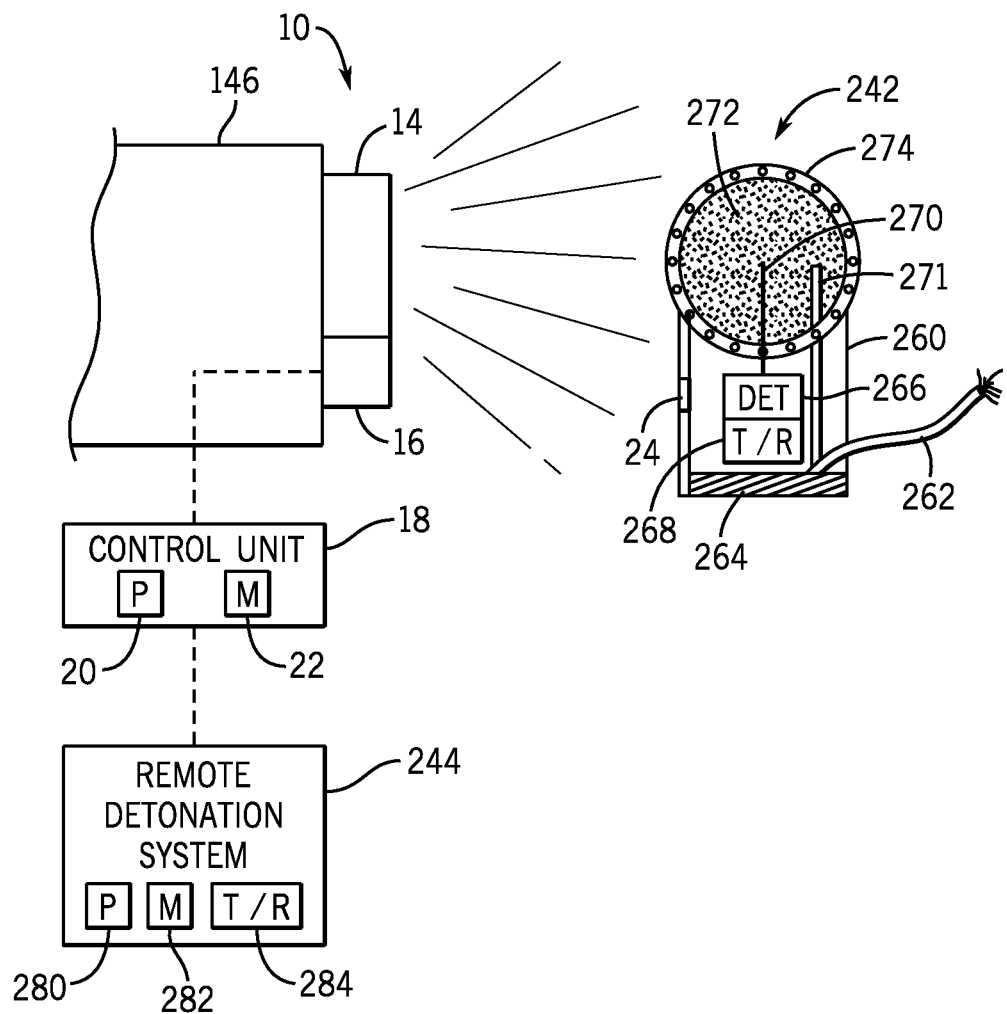
Figure 18:
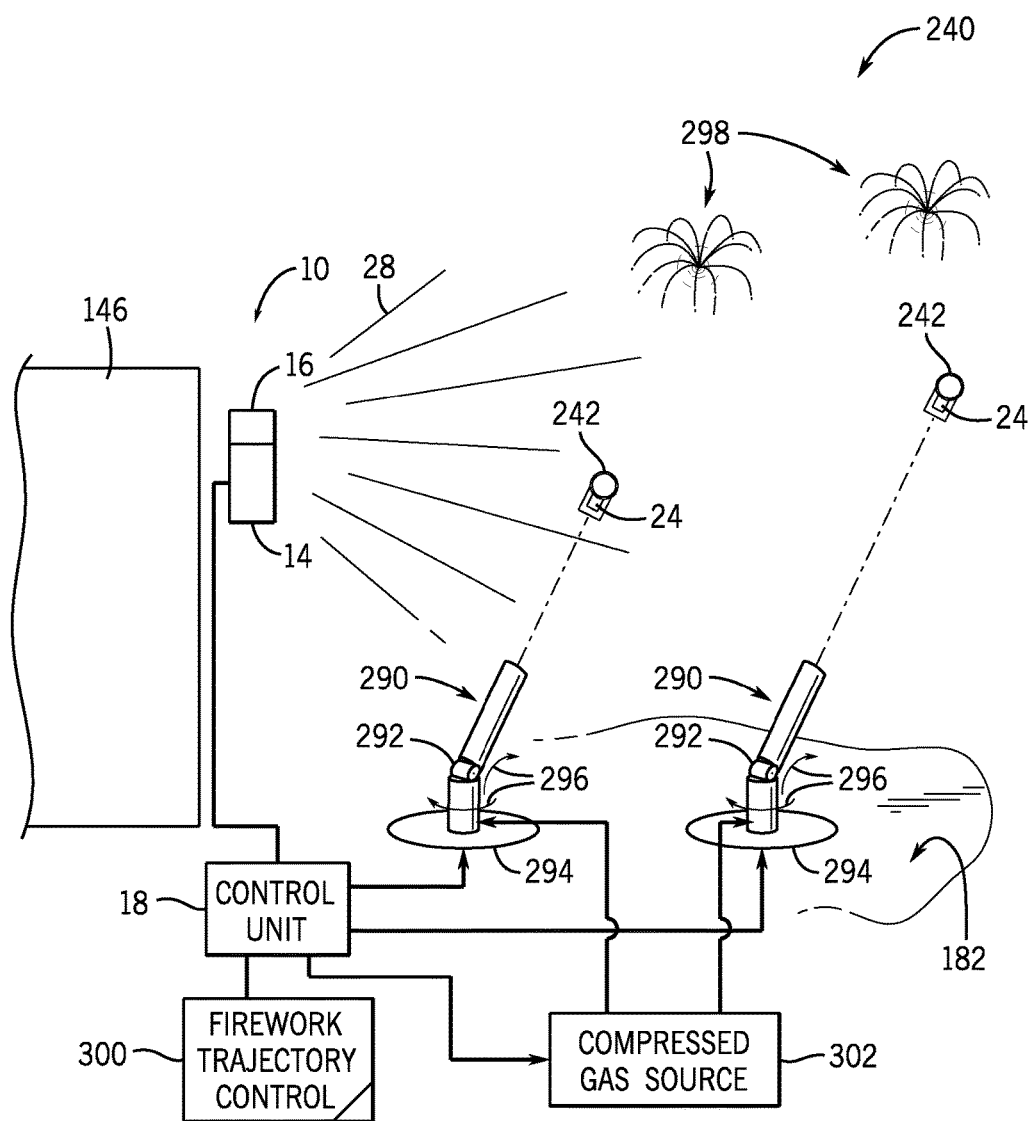

FIG. 17 is a cross-sectional side view of an ordinance having an electronic detonator and a retro-reflective marker attached to its outer casing to enable the ordinance to be tracked by the tracking system of FIG. 1, in accordance with an embodiment of the present disclosure; and FIG. 18 is a perspective view of a firework show using robotically-actuated cannons that are controlled by the tracking system of FIG. 1, in accordance with an embodiment of the present disclosure.

DETAILED DESCRIPTION

Generally, tracking systems may use a wide variety of inputs obtained from a surrounding environment to track certain objects. The source of the inputs may depend, for instance, on the type of tracking being performed and the capabilities of the tracking system. For example, tracking systems may use sensors disposed in an environment to actively generate outputs received by a main controller. The controller may then process the generated outputs to determine certain information used for tracking. One example of such tracking may include tracking the motion of an object to which a sensor is fixed. Such a system might also utilize one or more devices used to bathe an area in electromagnetic radiation, a magnetic field, or the like, where the electromagnetic radiation or magnetic field is used as a reference against which the sensor's output is compared by the controller. As may be appreciated, such active systems, if implemented to track a large number of objects or even people, could be quite expensive to employ and processor-intensive for the main controller of the tracking system.

Other tracking systems, such as certain passive tracking systems, may perform tracking without providing an illumination source or the like. For instance, certain tracking systems may use one or more cameras to obtain outlines or rough skeletal estimates of objects, people, and so forth. However, in situations where background illumination may be intense, such as outside on a hot and sunny day, the accuracy of such a system may be reduced due to varying degrees of noise received by detectors of the passive tracking system.

With the foregoing in mind, it is now recognized that traditional tracking systems have certain disadvantages and that improved tracking systems are desired for use in a variety of contexts, including amusement park attractions, workplace monitoring, sports, and security systems, among others. For instance, it is presently recognized that improved tracking systems may be utilized to enhance operations in a variety of amusement park settings and other entertainment attractions.

In accordance with one aspect of the present disclosure, a dynamic signal to noise ratio tracking system uses emitted electromagnetic radiation and, in some embodiments, retro-reflection, to enable detection of markers and/or objects within the field of view of the tracking system. The disclosed tracking system may include an emitter configured to emit electromagnetic radiation in a field of view, a sensing device configured to detect the electromagnetic radiation retro-reflected back from objects within the field of view, and a controller configured to perform various processing and analysis routines including interpreting signals from the sensing device and controlling automated equipment based on the detected locations of the objects or markers. The disclosed tracking system may also be configured to track several different objects at the same time (using the same emission and detection features). In some embodiments, the tracking system tracks a location of retro-reflective markers placed on the objects to estimate a location of the objects. As used herein, retro-reflective markers are reflective markers designed to retro-reflect electromagnetic radiation approximately back in the direction from which the electromagnetic radiation was emitted. More specifically, retro-reflective markers used in accordance with the present disclosure, when illuminated, reflect electromagnetic radiation back toward the source of emission in a narrow cone. In contrast, certain other reflective materials, such as shiny materials, may undergo diffuse reflection where electromagnetic radiation is reflected in many directions. Further still, mirrors, which also reflect electromagnetic radiation, do not typically undergo retro-reflection. Rather, mirrors undergo specular reflection, where an angle of electromagnetic radiation (e.g., light such as infrared, ultraviolet, visible, or radio waves and so forth) incident onto the mirror is reflected at an equal but opposite angle (away from the emission source).

Retro-reflective materials used in accordance with the embodiments set forth below can be readily obtained from a number of commercial sources. One example includes retro-reflective tape, which may be fitted to a number of different objects (e.g., environmental features, clothing items, toys). Due to the manner in which retro-reflection occurs using such markers in combination with the detectors 16 used in accordance with the present disclosure, the retro-reflective markers cannot be washed out by the sun or even in the presence of other emitters that emit electromagnetic radiation in wavelengths that overlap with the wavelengths of interest. Accordingly, the disclosed tracking system may be more reliable, especially in an outdoor setting and in the presence of other electromagnetic emission sources, compared to existing optical tracking systems.

While the present disclosure is applicable to a number of different contexts, presently disclosed embodiments are directed to, among other things, various aspects relating to tracking changes to certain structures (e.g., building, support columns) within an amusement park, and, in some situations, controlling amusement park equipment (e.g., automated equipment) based on information obtained from such a dynamic signal to noise ratio tracking system. Indeed, it is presently recognized that by using the disclosed tracking systems, reliable and efficient amusement park operations may be carried out, even though there are a number of moving objects, guests, employees, sounds, lights, and so forth, in an amusement park, which could otherwise create high levels of noise for other tracking systems, especially other optical tracking systems that do not use retro-reflective markers in the manner disclosed herein.

In certain aspects of the present disclosure, a control system of the amusement park (e.g., a control system associated with a particular area of the amusement park, such as a ride) may use information obtained by the dynamic signal to noise ratio tracking system to monitor and evaluate information relating to people, machines, vehicles (e.g., guest vehicles, service vehicles), and similar features in the area to provide information that may be useful in the more efficient operation of amusement park operations. For example, the information may be used to determine whether certain automated processes may be triggered or otherwise allowed to proceed. The evaluated information pertaining to vehicles in the amusement park may include, for instance, a location, a movement, a size, or other information relating to automated machines, ride vehicles, and so forth, within certain areas of the amusement park. By way of non-limiting example, the information may be evaluated to track people and machines to provide enhanced interactivity between the people and the machines, to track and control unmanned aerial vehicles, to track and control ride vehicles and any show effects associated with the ride vehicle, and so forth.

Certain aspects of the present disclosure may be better understood with reference to FIG. 1, which generally illustrates the manner in which a dynamic signal to noise ratio tracking system 10 (hereinafter referred to as "tracking system 10") may be integrated with amusement park equipment 12 in accordance with present embodiments. As illustrated, the tracking system 10 includes an emitter 14 (which may be all or a part of an emission subsystem having one or more emission devices and associated control circuitry) configured to emit one or more wavelengths of electromagnetic radiation (e.g., light such as infrared, ultraviolet, visible, or radio waves and so forth) in a general direction. The tracking system 10 also includes a detector 16 (which may be all or a part of a detection subsystem having one or more sensors, cameras, or the like, and associated control circuitry) configured to detect electromagnetic radiation reflected as a result of the emission, as described in further detail below.

To control operations of the emitter 14 and detector 16 (emission subsystem and detection subsystem) and perform various signal processing routines resulting from the emission, reflection, and detection process, the tracking system 10 also includes a control unit 18 communicatively coupled to the emitter 14 and detector 16. Accordingly, the control unit 18 may include one or more processors 20 and one or more memory 22, which may generally referred to herein as "processing circuitry." By way of specific but non-limiting example, the one or more processors 20 may include one or more application specific integrated circuits (ASICs), one or more field programmable gate arrays (FPGAs), one or more general purpose processors, or any combination thereof. Additionally, the one or more memory 22 may include volatile memory, such as random access memory (RAM), and/or non-volatile memory, such as read-only memory (ROM), optical drives, hard disc drives, or solid-state drives. In some embodiments, the control unit 18 may form at least a portion of a control system configured to coordinate operations of various amusement park features, including the equipment 12. As described below, such an integrated system may be referred to as an amusement park attraction and control system.

The tracking system 10 is specifically configured to detect a position of an illuminated component, such as a retro-reflective marker 24 having a properly correlated retro-reflective material relative to a grid, pattern, the emission source, stationary or moving environmental elements, or the like. In some embodiments, the tracking system 10 is designed to utilize the relative positioning to identify whether a correlation exists between one or more such illuminated components and a particular action to be performed by the amusement park equipment 12, such as triggering of a show effect, dispatch of a ride vehicle, closure of a gate, synchronization of security cameras with movement, and so on. More generally, the action may include the control of machine movement, image formation or adaptation, and similar processes.

As illustrated, the retro-reflective marker 24 is positioned on an object 26, which may correspond to any number of static or dynamic features. For instance, the object 26 may represent boundary features of an amusement park attraction, such as a floor, a wall, a gate, or the like, or may represent an item wearable by a guest, park employee, or similar object. Indeed, as set forth below, within an amusement park attraction area, many such retro-reflective markers 24 may be present, and the tracking system 10 may detect reflection from some or all of the markers 24, and may perform various analyses based on this detection.

Referring now to the operation of the tracking system 10, the emitter 14 operates to emit electromagnetic radiation, which is represented by an expanding electromagnetic radiation beam 28 electromagnetic radiation beam 28 electromagnetic radiation beam 28 for illustrative purposes, to selectively illuminate, bathe, or flood a detection area 30 in the electromagnetic radiation. Electromagnetic radiation beam 28 is intended to generally represent any form of electromagnetic radiation that may be used in accordance with present embodiments, such as forms of light (e.g., infrared, visible, UV) and/or other bands of the electromagnetic spectrum (e.g., radio waves and so forth). However, it is also presently recognized that, in certain embodiments, it may be desirable to use certain bands of the electromagnetic spectrum depending on various factors. For example, in one embodiment, it may be desirable to use forms of electromagnetic radiation that are not visible to the human eye or within an audible range of human hearing, so that the electromagnetic radiation used for tracking does not distract guests from their experience. Further, it is also presently recognized that certain forms of electromagnetic radiation, such as certain wavelengths of light (e.g., infrared) may be more desirable than others, depending on the particular setting (e.g., whether the setting is "dark," or whether people are expected to cross the path of the beam). Again, the detection area 30 may correspond to all or a part of an amusement park attraction area, such as a stage show, a ride vehicle loading area, a waiting area outside of an entrance to a ride or show, and so forth.

The electromagnetic radiation beam 28, in certain embodiments, may be representative of multiple light beams (beams of electromagnetic radiation) being emitted from different sources (all part of an emission subsystem). Further, in some embodiments the emitter 14 is configured to emit the electromagnetic radiation beam 28 at a frequency that has a correspondence to a material of the retro-reflective marker 24 (e.g., is able to be reflected by the retro-reflective elements of the marker 24). For instance, the retro-reflective marker 24 may include a coating of retro-reflective material disposed on a body of the object 26 or a solid piece of material coupled with the body of the object 26. By way of more specific but non-limiting example, the retro-reflective material may include spherical and/or prismatic reflective elements that are incorporated into a reflective material to enable retro-reflection to occur. Again, in certain embodiments many such retro-reflective markers 24 may be present, and may be arranged in a particular pattern stored in the memory 22 to enable further processing, analysis, and control routines to be performed by the control unit 18 (e.g., control system).

The retro-reflective marker 24 may reflect a majority of the electromagnetic radiation (e.g., infrared, ultraviolet, visible wavelengths, or radio waves and so forth) incident from the electromagnetic radiation beam 28 back toward the detector 16 within a relatively well-defined cone having a central axis with substantially the same angle as the angle of incidence. This reflection facilitates identification of a location of the retro-reflective marker 24 by the system 10 and correlation thereof to various information stored in the memory 22 (e.g., patterns, possible locations). This location information (obtained based on the reflected electromagnetic radiation) may then be utilized by the control unit 18 to perform various analysis routines and/or control routines, for example to determine whether to cause triggering or other control of the amusement park equipment 12.

Specifically, in operation, the detector 16 of the system 10 may function to detect the electromagnetic radiation beam 28 retro-reflected from the retro-reflective marker 24 and provide data associated with the detection to the control unit 18 via communication lines 31 for processing. The detector 16 may operate to specifically identify the marker 24 based on certain specified wavelengths of electromagnetic radiation emitted and reflected and, thus, avoid issues with false detections. For example, the detector 16 may be specifically configured to detect certain wavelengths of electromagnetic radiation (e.g., corresponding to those emitted by the emitter 14) through the use of physical electromagnetic radiation filters, signal filters, and the like. Further, the detector 16 may utilize a specific arrangement of optical detection features and electromagnetic radiation filters to capture substantially only retro-reflected electromagnetic radiation.

For example, the detector 16 may be configured to detect wavelengths of electromagnetic radiation retro-reflected by the retro-reflective markers 24 while filtering wavelengths of electromagnetic radiation not retro-reflected by the markers 24, including those wavelengths of interest. Thus, the detector 16 may be configured to specifically detect (e.g., capture) retro-reflected electromagnetic radiation while not detecting (e.g., capturing) electromagnetic radiation that is not retro-reflected. In one embodiment, the detector 16 may utilize the directionality associated with retro-reflection to perform this selective filtering. Accordingly, while the detector 16 receives electromagnetic radiation from a variety of sources (including spuriously reflected electromagnetic radiation, as well as environmental electromagnetic radiation), the detector 16 is specifically configured to filter out all or substantially all spuriously reflected signals while retaining all or substantially all intended signals. Thus, the signal-to-noise ratio of signals actually processed by the detector 16 and control unit 18 is very high, regardless of the signal-to-noise ratio that exists for the electromagnetic bands of interest outside of the detector 16.

For example, the detector 16 may receive retro-reflected electromagnetic radiation (e.g., from the retro-reflective markers 24) and ambient electromagnetic radiation from within an area (e.g., guest attraction area). The ambient electromagnetic radiation may be filtered, while the retro-reflected electromagnetic radiation, which is directional, may not be filtered (e.g., may bypass the filter). Thus, in certain embodiments, the "image" generated by the detector 16 may include a substantially dark (e.g., black or blank) background signal, with substantially only retro-reflected electromagnetic radiation producing contrast.

In accordance with certain embodiments, the retro-reflected electromagnetic radiation may include different wavelengths that are distinguishable from one another. In one embodiment, the filters of the detector 16 may have optical qualities and may be positioned within the detector such that the optical detection devices of the detector 16 substantially only receive electromagnetic wavelengths retro-reflected by the retro-reflective markers 24 (or other retro-reflective elements), as well as any desired background wavelengths (which may provide background or other landscape information). To produce signals from the received electromagnetic radiation, as an example, the detector 16 may be a camera having a plurality of electromagnetic radiation capturing features (e.g., charge-coupled devices (CCDs) and/or complementary metal oxide semiconductor (CMOS) sensors corresponding to pixels). In one example embodiment, the detector 16 may be an Amp® high dynamic range (HDR) camera system available from Contrast Optical Design and Engineering, Inc. of Albuquerque, N. Mex.

Because retro-reflection by the retro-reflective markers 24 is such that a cone of reflected electromagnetic radiation is incident on the detector 16, the control unit 18 may in turn correlate a center of the cone, where the reflected electromagnetic radiation is most intense, to a point source of the reflection. Based on this correlation, the control unit 18 may identify and track a location of this point source, or may identify and monitor a pattern of reflection by many such retro-reflective markers 24.

For instance, once the control unit 18 receives the data from the detector 16, the control unit 18 may employ known visual boundaries or an established orientation of the detector 16 to identify a location (e.g., coordinates) corresponding to the detected retro-reflective marker 24. When multiple stationary retro-reflective markers 24 are present, the control unit 18 may store known positions (e.g., locations) of the retro-reflective markers 24 to enable reflection pattern monitoring. By monitoring a reflection pattern, the control unit 18 may identify blockage (occlusion) of certain retro-reflective markers 24 by various moving objects, guests, employees, and so forth. It should also be noted that the bases for these comparisons may be updated based on, for example, how long a particular retro-reflective marker 24 has been positioned and used in its location. For instance, the stored pattern of reflection associated with one of the markers 24 may be updated periodically during a calibration stage, which includes a time period during which no objects or people are expected to pass over the marker 24. Such re-calibrations may be performed periodically so that a marker that has been employed for an extended period of time and has lost its retro-reflecting capability is not mistaken for a detected occlusion event.

In other embodiments, in addition to or in lieu of tracking one or more of the retro-reflective markers 24, the tracking system 10 may be configured to detect and track various other objects located within the detection area 30. Such objects 32 may include, among other things, ride vehicles, people (e.g., guests, employees), and other moving park equipment. For example, the detector 16 of the system 10 may function to detect the electromagnetic radiation beam 28 bouncing off of an object 32 (without retro-reflective markers 24) and provide data associated with this detection to the control unit 18. That is, the detector 16 may detect the object 32 based entirely on diffuse or specular reflection of electromagnetic energy off the object 32. In some embodiments, the object 32 may be coated with a particular coating that reflects the electromagnetic radiation beam 28 in a detectable and predetermined manner. Accordingly, once the control unit 18 receives the data from the detector 16, the control unit 18 may determine that the coating associated with the object 32 reflected the electromagnetic radiation, and may also determine the source of the reflection to identify a location of the object 32.

Whether the retro-reflective markers 24 are stationary or moving, the process of emitting the electromagnetic radiation beam 28, sensing of the reflected electromagnetic radiation from the retro-reflective markers 24 (or objects 32 with no or essentially no retro-reflective material), and determining a location of the retro-reflective marker 24 or object 32 may be performed by the control unit 18 numerous times over a short period. This process may be performed at distinct intervals, where the process is initiated at predetermined time points, or may be performed substantially continuously, such that substantially immediately after the process is completed, it is re-initiated. In embodiments where the retro-reflective markers 24 are stationary and the control unit 18 performs retro-reflective pattern monitoring to identify marker blockage, the process may be performed at intervals to obtain a single retro-reflective pattern at each interval. This may be considered to represent a single frame having a reflection pattern corresponding to a pattern of blocked and unblocked retro-reflective markers 24.

On the other hand, such procedures may essentially be performed continuously to facilitate identification of a path and/or trajectory through which the retro-reflective marker 24 has moved. The marker 24, moving within the detection area 30, would be detected over a particular timeframe or simply in continuous series. Here, the pattern of reflection would be generated and identified over a time period.

In accordance with the embodiments set forth above, the detector 16 and control unit 18 may operate on a variety of different timeframes depending on the tracking to be performed and the expected movement of the tracked object through space and time. As an example, the detector 16 and the control unit 18 may operate in conjunction to complete all logical processes (e.g., updating analysis and control signals, processing signals) in the time interval between the capture events of the detector 16. Such processing speeds may enable substantially real-time tracking, monitoring, and control where applicable. By way of non-limiting example, the detector capture events may be between approximately 1/60 of a second and approximately 1/30 of a second, thus generating between 30 and 60 frames per second. The detector 16 and the control unit 18 may operate to receive, update, and process signals between the capture of each frame. However, any interval between capture events may be utilized in accordance with certain embodiments.

Once a particular pattern of retro-reflection has been detected, a determination may be made by the control unit 18 as to whether the pattern correlates to a stored pattern identified by the control unit 18 and corresponding to a particular action to be performed by the amusement park equipment 12. For example, the control unit 18 may perform a comparison of a position, path, or trajectory of the retro-reflective marker 24 with stored positions, paths, or trajectories to determine an appropriate control action for the equipment 12. Additionally or alternatively, as described in further detail below, the control unit 18 may determine whether a particular pattern obtained at a particular time point correlates to a stored pattern associated with a particular action to be performed by the amusement park equipment 12. Further still, the control unit 18 may determine whether a set of particular patterns obtained at particular time points correlate to a stored pattern change associated with a particular action to be performed by the amusement park equipment 12.

While the control unit 18 may cause certain actions to be automatically performed within the amusement park in the manner set forth above, it should be noted that similar analyses to those mentioned above may also be applied to the prevention of certain actions (e.g., where the park equipment 12 blocks action or is blocked from performing an action). For example, in situations where a ride vehicle can be automatically dispatched, the control unit 18, based upon tracking changes in the retro-reflective markers 24, may halt automatic dispatching, or may even prevent dispatching by a ride operator until additional measures are taken (e.g., additional confirmations that the ride vehicle is cleared for departure). This type of control may be applied to other amusement park equipment, as well. For example, flame effects, fireworks, or similar show effects may be blocked from being triggered, may be stopped, or may be reduced in intensity, due to intervention by the control unit 18 as a result of certain pattern determinations as described herein.

Having generally described the configuration of the system 10, it should be noted that the arrangement of the emitter 14, detector 16, control unit 18, and other features may vary based on application-specific considerations and the manner in which the control unit 18 performs evaluations based on electromagnetic radiation from the retro-reflective markers 24. In the embodiment of the tracking system 10 illustrated in FIG. 1, the emitter 14 and the sensor or detector 16 are integral features such that a plane of operation associated with the detector 16 is essentially overlapping with a plane of operation associated with the emitter 14. That is, the detector 16 is located in substantially the same position as the emitter 14, which may be desirable due to the retro-reflectivity of the markers 24. However, the present disclosure is not necessarily limited to this configuration. For instance, as noted above, retro-reflection may be associated with a cone of reflection, where the highest intensity is in the middle of the reflected cone. Accordingly, the detector 16 may be positioned within an area where the reflected cone of the retro-reflective markers is less intense than its center, but may still be detected by the detector 16.

Figure 2:
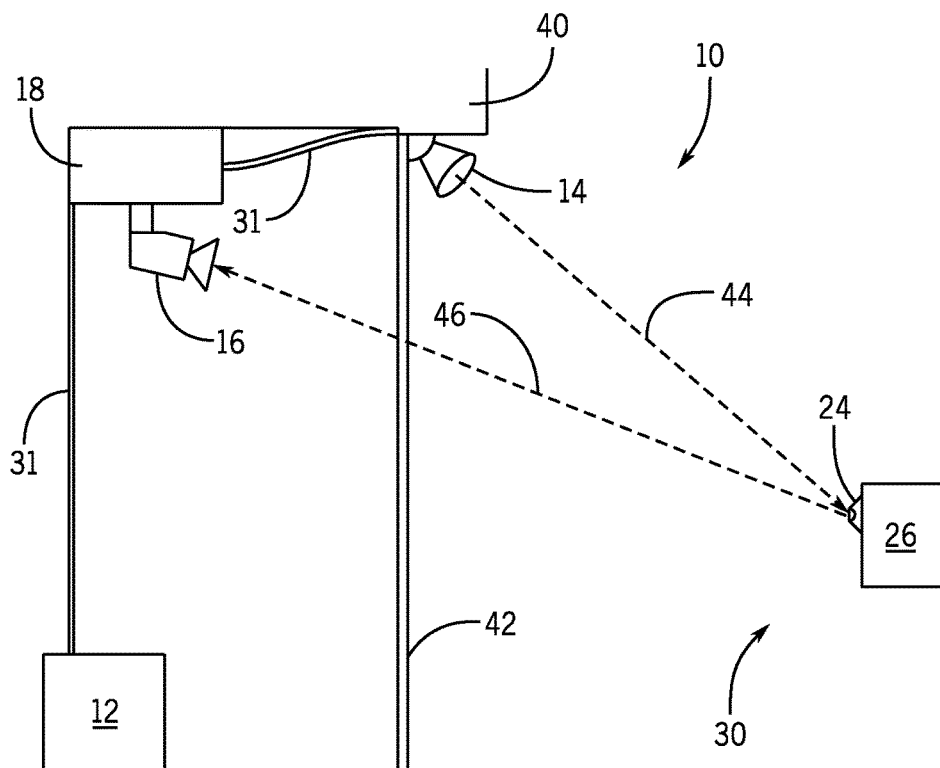
FIG. 2 is a schematic diagram of another tracking system utilizing a dynamic signal to noise ratio device to track objects, in accordance with an embodiment of the present disclosure.

By way of non-limiting example, in some embodiments, the emitter 14 and the detector 16 may be concentric. However, the detector 16 (e.g., an infrared camera) may be positioned in a different location with respect to the emitter 14, which may include an infrared light bulb, one or more diode emitters, or similar source. As illustrated in FIG. 2, the emitter 14 and detector 16 are separate and are positioned at different locations on an environmental feature 40 of an amusement attraction area (e.g., a wall or ceiling). Specifically, the emitter 14 of FIG. 2 is positioned outside of a window 42 of a storefront containing other components of the system 10. The detector 16 of FIG. 2 is positioned away from the emitter 14, but is still oriented to detect electromagnetic radiation reflected from the retro-reflective marker 24 and originating from the emitter 14.

For illustrative purposes, arrows 44, 46 represent a light beam (a beam of electromagnetic radiation) being emitted from the emitter 14 (arrow 44) into the detection area 30, retro-reflected by the retro-reflective marker 24 on the object 26 (arrow 46), and detected by the detector 16. The light beam represented by the arrow 44 is merely one of numerous electromagnetic radiation emissions (light beams) that flood or otherwise selectively illuminate the detection area 30 from the emitter 14. It should be noted that still other embodiments may utilize different arrangements of components of the system 10 and implementations in different environments in accordance with the present disclosure.

Having now discussed the general operation of the tracking system 10 to detect a position of retro-reflective markers 24 and/or objects 32, as illustrated in FIG. 1, certain applications of the tracking system 10 will be described in further detail below. For example, it may be desirable to track the locations of people within a particular area through the use of the disclosed tracking systems. This may be useful, for example, for controlling lines in a ride vehicle loading area, controlling access to different areas, determining appropriate instances when show effects can be triggered, determining appropriate instances when certain automated machinery can be moved, and may also be useful for assisting a live show performance (e.g., blocking actors on a stage). That is, during performances, actors are supposed to be standing at particular positions on the stage at certain times. To ensure that the actors are hitting their appropriate positions at the right time, the tracking system 10 may be installed above the stage and used to track the positions and/or motion of all the actors on the stage. Feedback from the tracking system 10 may be utilized to evaluate how well the actors are hitting the desired spots on the stage.

In addition to blocking on a stage, the tracking system 10 may be used in contexts that involve tracking and/or evaluating shoppers in a store or other commercial setting. That is, a store may be outfitted with the disclosed tracking systems 10 in order to determine where guests are spending time within the store. Instead of triggering a show effect, such tracking systems 10 may be used to monitor the flow of people within the store and control the availability of certain items as a result, control the flow of movement of people, etc. For instance, information collected via the disclosed tracking systems 10 may be used to identify and evaluate which setups or displays within the store are most attractive, to determine what items for sale are the most popular, or to determine which areas of the store, if any, are too crowded. This information may be analyzed and used to improve the store layout, product development, and crowd management, among other things.

It should be noted that other applications may exist for tracking positions of people, objects, machines, etc. within an area other than those described above. Presently disclosed tracking systems 10 may be configured to identify and/or track the position and movement of people and/or objects within the detection area 30. The tracking system 10 may accomplish this tracking in several different ways, which were introduced above and are explained in further detail below. It should be noted that the tracking system 10 is configured to detect a position of one or more people, one or more objects 32, or a combination of different features, at the same time in the same detection area 30 using the single emitter 14, detector 16, and control unit 18. However, the use of multiple such emitters 14, detectors 16, and control units 18 is also within the scope of the present disclosure. Accordingly, there may be one or more of the emitters 14 and one or more of the detectors 16 in the detection area 30. Considerations such as the type of tracking to be performed, the desired range of tracking, for redundancy, and so forth, may at least partially determine whether multiple or a single emitter and/or detector are utilized.

For instance, as noted above, the tracking system 10 may generally be configured to track a target moving in space and in time (e.g., within the detection area 30 over time). When a single detection device (e.g., detector 16) is utilized, the tracking system 10 may monitor retro-reflected electromagnetic radiation from a defined orientation to track a person, object, etc. Because the detector 16 has only one perspective, such detection and tracking may, in some embodiments, be limited to performing tracking in only one plane of movement (e.g., the tracking is in two spatial dimensions). Such tracking may be utilized, as an example, in situations where the tracked target has a relatively low number of degrees of freedom, such as when movement is restricted to a constrained path (e.g., a track). In one such embodiment, the target has a determined vector orientation.

On the other hand, when multiple detection devices are utilized (e.g., two or more of the detectors 16) to track a target in both space and time, the tracking system 10 may monitor retro-reflected electromagnetic radiation from multiple orientations. Using these multiple vantage points, the tracking system 10 may be able to track targets having multiple degrees of freedom. In other words, the use of multiple detectors may provide both vector orientation and range for the tracked target. This type of tracking may be particularly useful in situations where it may be desirable to allow the tracked target to have unrestricted movement in space and time.

Multiple detectors may also be desirable for redundancy in the tracking. For example, multiple detection devices applied to scenarios where movement of the target is restricted, or not, may enhance the reliability of the tracking performed by the tracking system 10. The use of redundant detectors 16 may also enhance tracking accuracy, and may help prevent geometric occlusion of the target by complex geometric surfaces, such as winding pathways, hills, folded clothing, opening doors, and so on.

Figure 3:
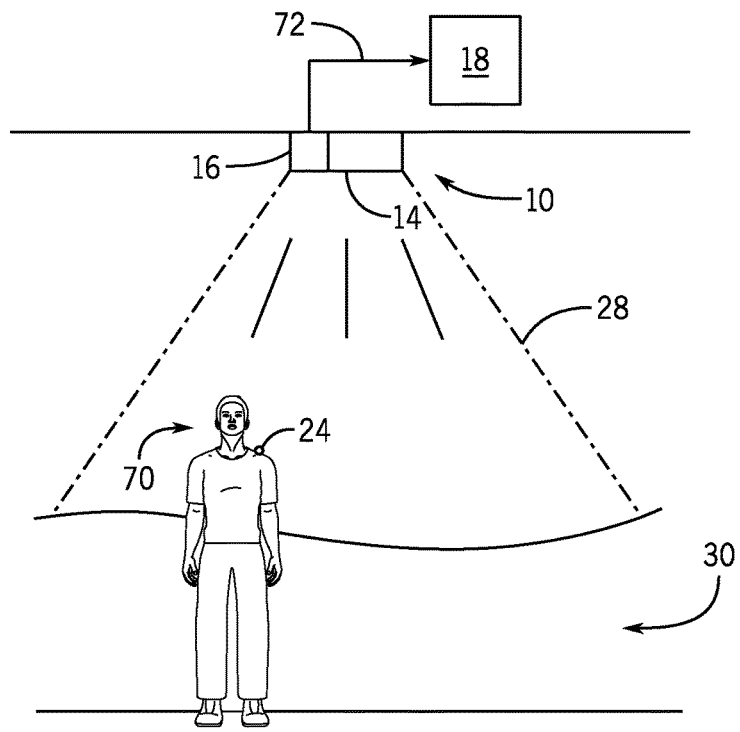
FIG. 3 is a schematic view of the tracking system of FIG. 1 tracking a retro-reflective marker on a person, in accordance with an embodiment of the present disclosure.

In accordance with one aspect of the present disclosure, the tracking system 10 may track relative positions of multiple targets (e.g., people, objects, machines) positioned within the detection area 30 through the use of the retro-reflective markers 24. As illustrated in FIG. 3, the retro-reflective markers 24 may be disposed on a person 70. Additionally or alternatively, the marker 24 may be positioned on a machine or other object (e.g., object 26). Accordingly, the techniques disclosed herein for tracking movement of the person 70 in space and time may also be applied to movement of an object in the amusement park, either in addition to the person 70 or as an alternative to the person 70. In such embodiments, the marker 24 may be positioned on an outside of the object 26 (e.g., a housing), as shown in FIG. 1.

In the illustrated embodiment of FIG. 3, the retro-reflective marker 24 is disposed on the outside of the person's clothing. For instance, the retro-reflective marker 24 may be applied as a strip of retro-reflective tape applied to an armband, headband, shirt, personal identification feature, or other article. Additionally or alternatively, the retro-reflective marker 24 may, in some embodiments, be sewn into clothing or applied to the clothing as a coating. The retro-reflective marker 24 may be disposed on the clothing of the person 70 in a position that is accessible to the electromagnetic radiation beam 28 being emitted from the emitter 14. As the person 70 walks about the detection area 30 (in the case of the object 32, the object 32 may move through the area 30), the electromagnetic radiation beam 28 reflects off the retro-reflective marker 24 and back to the detector 16. The detector 16 communicates with the control unit 18 by sending a signal 72 to the processor 20, this signal 72 being indicative of the reflected electromagnetic radiation detected via the detector 16. The tracking system 10 may interpret this signal 72 to track the position or path of the person 70 (or object 32) moving about a designated area (i.e., track the person or object in space and time). Again, depending on the number of detectors 16 utilized, the control unit 18 may determine vector magnitude, orientation, and sense of the person and/or object's movement based on the retro-reflected electromagnetic radiation received.

Figure 4:
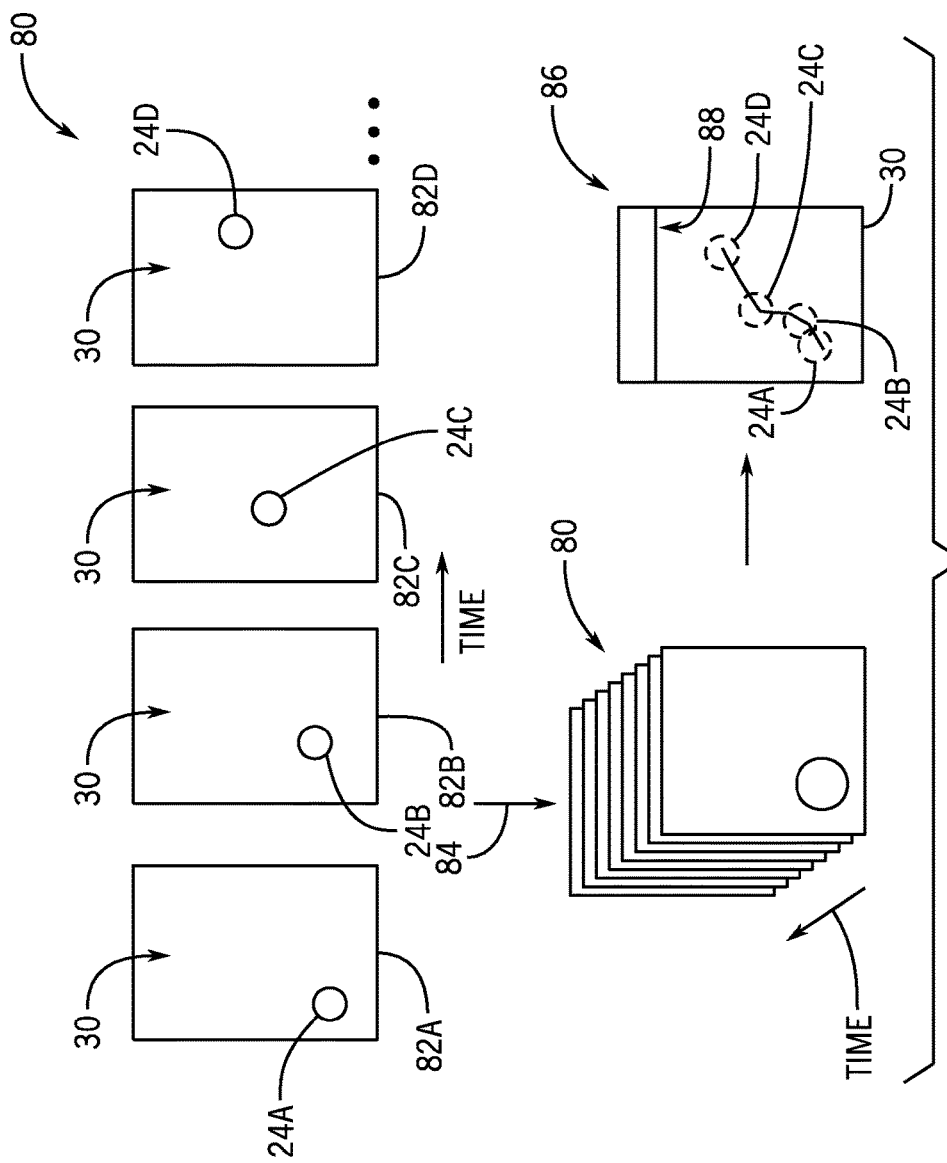
FIG. 4 is a schematic representation of an analysis performed by the tracking system of FIG. 1 in which position and movement of a person or object is tracked in space and time, in accordance with an embodiment of the present disclosure.

The tracking of the person 70 (which may also be representative of a moving object) is illustrated schematically in FIG. 4. More specifically, FIG. 4 illustrates a series 80 of frames 82 captured by the detector 16 (e.g., camera) over a period of time. As noted above, a plurality of such frames (e.g., between 30 and 60) may be generated every second in certain embodiments. It should be noted that FIG. 4 may not be an actual representation of outputs produced by the tracking system 10, but is described herein to facilitate an understanding of the tracking and monitoring performed by the control unit 18. The frames 82 each represent the detection area 30, and the position of the retro-reflective marker 24 within the area 30. Alternatively, the frames 82 may instead represent marker blockage within the area 30, for example where a grid of markers 24 are occluded by an object or person.

As shown, a first frame 82A includes a first instance of the retro-reflective marker, designated as 24A, having a first position. As the series 80 progresses in time, a second frame 82B includes a second instance of the retro-reflective marker 24B, which is displaced relative to the first instance, and so on (thereby producing third and fourth instances of the retro-reflective marker 24C and 24D). After a certain period of time, the control unit 18 has generated the series 80, where the operation of generating the series 80 is generally represented by arrow 84.

The series 80 may be evaluated by the control unit 18 in a number of different ways. In accordance with the illustrated embodiment, the control unit 18 may evaluate movement of the person 70 or object 32 by evaluating the positions of the marker 24 (or blockage of certain markers) over time. For example, the control unit 18 may obtain vector orientation, range, and sense, relating to the movement of the tracked target depending on the number of detectors 16 utilized to perform the tracking. In this way, the control unit 18 may be considered to evaluate a composite frame 86 representative of the movement of the tracked retro-reflective marker 24 (or tracked blockage of markers 24) over time within the detection area 30. Thus, the composite frame 86 includes the various instances of the retro-reflective marker 24 (including 24A, 24B, 24C, 24D), which may be analyzed to determine the overall movement of the marker 24 (and, therefore, the person 70 and/or object 26, whichever the case may be).

As also illustrated in FIG. 4, this monitoring may be performed relative to certain environmental elements 88, which may be fixed within the detection area 30 and/or may be associated with reflective materials. The control unit 18 may perform operations not only based on the detected positions of the marker 24, but also based on extrapolated movement (e.g., a projected path of the retro-reflective marker 24 through the detection area 30 or projected positions of marker grid occlusion) in relation to the environmental elements 88.

Figure 5:
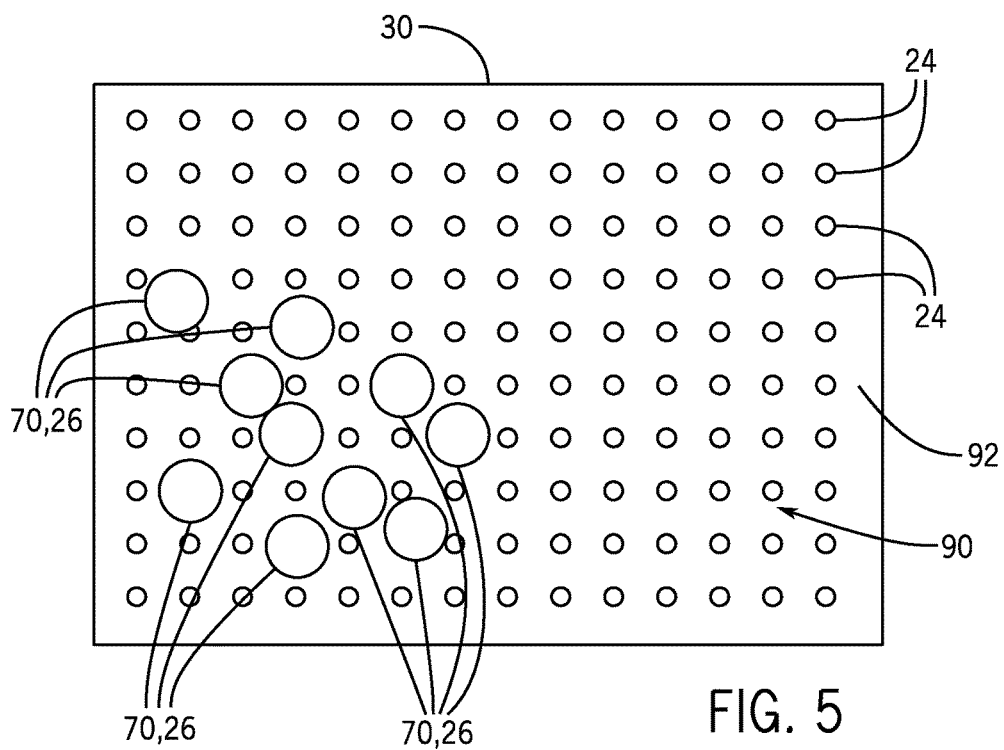
FIG. 5 is an overhead view of a room with a grid pattern of retro-reflective markers for tracking a position of people in the room via the tracking system of FIG. 1, in accordance with an embodiment of the present disclosure.

Another method for tracking one or more people 70 or objects 32 in an area is illustrated schematically in FIG. 5. Specifically, FIG. 5 represents an overhead view of a group of people 70 standing in the detection area 30. Although not illustrated, the tracking system 10 may be present directly above this detection area 30 in order to detect positions of people 70 (and other objects) present within the detection area 30 (e.g., to obtain a plan view of the detection area 30). In the illustrated embodiment, the retro-reflective markers 24 are positioned in a grid pattern 90 on a floor 92 of the detection area 30 (e.g., as a coating, pieces of tape, or similar attachment method). The retro-reflective markers 24 may be arranged in any desired pattern (e.g., grid, diamond, lines, circles, solid coating, etc.), which may be a regular pattern (e.g., repeating) or a random pattern.

This grid pattern 90 may be stored in the memory 22, and portions of the grid pattern 90 (e.g., individual markers 24) may be correlated to locations of certain environmental elements and amusement park features (e.g., the amusement park equipment 12). In this way, the position of each of the markers 24 relative to such elements may be known. Accordingly, when the markers 24 retro-reflect the electromagnetic radiation beam 28 to the detector 16, the location of the markers 24 that are reflecting may be determined and/or monitored by the control unit 18.

As illustrated, when the people 70 or objects 32 are positioned over one or more of the retro-reflective markers 24 on the floor 92, the occluded markers cannot reflect the emitted electromagnetic radiation back to the detector 16 above the floor 92. Indeed, in accordance with an embodiment, the grid pattern 90 may include retro-reflective markers 24 that are spaced apart by a distance that allows the people or objects positioned on the floor 92 to be detectable (e.g., blocking at least one of the retro-reflective markers 24). In other words, the distance between the markers 24 may be sufficiently small so that objects or people may be positioned over at least one of the retro-reflective markers 24.

In operation, the detector 16 may function to detect the electromagnetic radiation beam 28 retro-reflected from the retro-reflective markers 24 that are not covered up by people or objects located in the detection area 30. As discussed above, the detector 16 may then provide data associated with this detection to the control unit 18 for processing. The control unit 18 may perform a comparison of the detected electromagnetic radiation beam reflected off the uncovered retro-reflective markers 24 (e.g., a detected pattern) with stored positions of the completely uncovered grid pattern 90 (e.g., a stored pattern) and/or other known grid patterns resulting from blockage of certain markers 24. Based on this comparison, the control unit 18 may determine which markers 24 are covered to then approximate locations of the people 70 or objects 32 within the plane of the floor 92. Indeed, the use of a grid positioned on the floor 92 in conjunction with a single detector 16 may enable the tracking of movement in two dimensions. If higher order tracking is desired, additional grids and/or additional detectors 16 may be utilized. In certain embodiments, based on the locations of the people 70 or objects 32 in the detection area 30, the control unit 18 may adjust the operation of the amusement park equipment 12.

The process of emitting the electromagnetic radiation beam 28, sensing of the reflected electromagnetic radiation from the uncovered retro-reflective markers 24 on the floor 92, and determining a location of the people 70 may be performed by the control unit 18 numerous times over a short period in order to identify a series of locations of the people 70 moving about the floor 92 (to track motion of the group). Indeed, such procedures may essentially be performed continuously to facilitate identification of a path through which the people 70 have moved within the detection area 30 during a particular timeframe or simply in continuous series. Once the position or path one or more of the people 70 has been detected, the control unit 18 may further analyze the position or path to determine whether any actions should be performed by the equipment 12.

Figure 6:
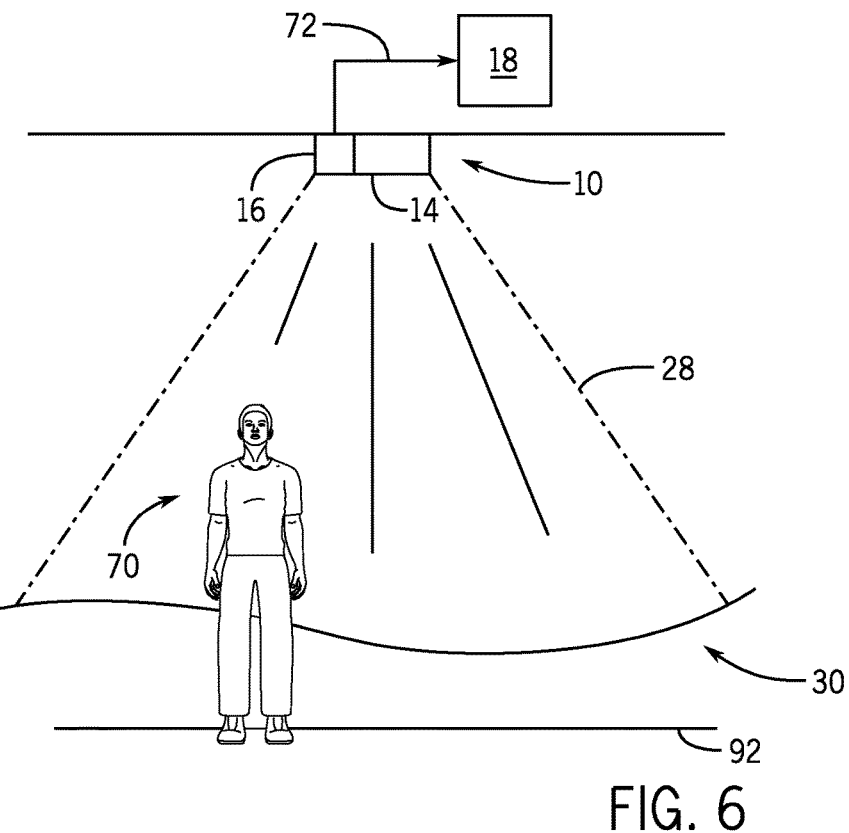
FIG. 6 is an elevational view of the tracking system of FIG. 1 tracking a person without tracking retro-reflective marker movement and without tracking retro-reflective marker occlusion, in accordance with an embodiment of the present disclosure.

As discussed in detail above with respect to FIG. 1, the control unit 18 may be configured to identify certain objects that are expected to cross the path of the electromagnetic radiation beam 28 within the detection area 30, including objects that are not marked with retro-reflective material. For example, as illustrated in FIG. 6, some embodiments of the tracking system 10 may be configured such that the control unit 18 is able to identify the person 70 (which is also intended to be representative of the object 32) located in the detection area 30, without the use of the retro-reflective markers 24. That is, the control unit 18 may receive data indicative of the electromagnetic radiation reflected back from the detection area 30, and the control unit 18 may compare a digital signature of the detected radiation to one or more possible data signatures stored in memory 22. That is, if the signature of electromagnetic radiation reflected back to the detector 16 matches closely enough to the signature of a person 70 or known object 32, then the control unit 18 may determine that the person 70 or object 32 is located in the detection area 30. For example, the control unit 18 may identify "dark spots," or regions where electromagnetic radiation was absorbed rather than reflected, within the detection area 30. These areas may have a geometry that the control unit 18 may analyze (e.g., by comparing to shapes, sizes, or other features of stored objects or people) to identify a presence, location, size, shape, etc., of an object (e.g., the person 70).

As may be appreciated with reference to FIGS. 1, 2, 3, and 6, the tracking system 10 may be positioned in a variety of locations to obtain different views of the detection area 30. Indeed, it is now recognized that different locations and combinations of locations of one or more of the tracking systems 10 (or one or more elements of the tracking system 10, such as multiple detectors 16) may be desirable for obtaining certain types of information relating to the retro-reflective markers 24 and the blockage thereof. For instance, in FIG. 1, the tracking system 10, and in particular the detector 16, is positioned to obtain an elevational view of at least the object 26 fitted with the retro-reflective marker 24 and the object 32. In FIG. 2, the detector 16 is positioned to obtain an overhead perspective view of the detection area 30, which enables detection of retro-reflective markers 24 positioned on a variety of environmental elements, moving objects, or people. In the embodiments of FIGS. 3 and 6, the detector 16 may be positioned to obtain a plan view of the detection area 30.

These different views may provide information that may be utilized by the control unit 18 for specific types of analyses and, in certain embodiments, control actions that may depend on the particular setting in which they are located. For example, in FIG. 7, the tracking system 10, and particularly the emitter 14 and the detector 16, are positioned to obtain a perspective view of the person 70 (or object 32) in the detection area 30. The detection area 30 includes the floor 92, but also includes a wall 93 on which the retro-reflective markers 24 are positioned to form the grid pattern 90. Here, the person 70 is blocking a subset of markers 24 positioned on the wall 93. The subset of markers 24 are unable to be illuminated by the emitter 14, are unable to retro-reflect the electromagnetic radiation back to the detector 16, or both, because the person 70 (also intended to represent an object) is positioned between the subset of markers 24 and the emitter 14 and/or detector 16.

The grid pattern 90 on the wall 93 may provide information not necessarily available from a plan view as shown in FIGS. 3 and 6. For example, the blockage of the retro-reflective markers 24 enables the control unit 18 to determine a height of the person 70, a profile of the person 70, or, in embodiments where there the object 32 is present, a size of the object 32, a profile of the object 32, and so forth. Such determinations may be made by the control unit 18 to evaluate whether the person 70 meets a height requirement for a ride, to evaluate whether the person 70 is associated with one or more objects 32 (e.g., bags, strollers), and may also be used to track movement of the person 70 or object 32 through the detection area 30 with a greater degree of accuracy compared to the plan view set forth in FIGS. 3 and 6. That is, the control unit 18 is better able to tie movement identified by blockage of the markers 24 to a particular person 70 by determining the person's profile, height, etc. Similarly, the control unit 18 is better able to track the movement of the object 32 through the detection area 30 by identifying the geometry of the object 32, and tying identified movement specifically to the object 32. In certain embodiments, tracking the height or profile of the person 70 may be performed by the tracking system 10 to enable the control unit 18 to provide recommendations to the person 70 based on an analysis of the person's evaluated height, profile, etc. Similar determinations and recommendations may be provided for objects 32, such as vehicles. For example, the control unit 18 may analyze a profile of guests at an entrance to a queue area for a ride. The control unit 18 may compare the overall size, height, etc., of the person 70 with ride specifications to warn individuals or provide a confirmation that they are able to ride the ride before spending time in the queue. Similarly, the control unit 18 may analyze the overall size, length, height, etc., of a vehicle to provide parking recommendations based on available space. Additionally or alternatively, the control unit 18 may analyze the overall size, profile, etc., of an automated piece equipment before allowing the equipment to perform a particular task (e.g., movement through a crowd of people).

The pattern 90 may also be positioned on both the wall 93 and the floor 92. Accordingly, the tracking system 10 may be able to receive retro-reflected electromagnetic radiation from markers 24 on the wall 93 and the floor 92, thereby enabling detection of marker blockage and monitoring of movement in three dimensions. Specifically, the wall 93 may provide information in a height direction 94, while the floor 92 may provide information in a depth direction 96. Information from both the height direction 94 and the depth direction 96 may be correlated to one another using information from a width direction 98, which is available from both the plan and elevational views.

Indeed, it is now recognized that if two objects 32 or people 70 overlap in the width direction 98, they may be at least partially resolved from one another using information obtained from the depth direction 96. Further, it is also now recognized that the use of multiple emitters 14 and detectors 16 in different positions (e.g., different positions in the width direction 98) may enable resolution of height and profile information when certain information may be lost or not easily resolved when only one emitter 14 and detector 16 are present. More specifically, using only one emitter 14 and detector 16 may result in a loss of certain information if there is overlap between objects 32 or people 70 in the width direction 98 (or, more generally, overlap in a direction between the markers 24 on the wall 93 and the detector 16). However, embodiments using multiple (e.g., at least two) detectors 16 and/or emitters 14 may cause distinct retro-reflective patterns to be produced by the markers 24 and observed from the detectors 16 and/or emitters 14 positioned at different perspectives. Indeed, because the markers 24 are retro-reflective, they will retro-reflect electromagnetic radiation back toward the electromagnetic radiation source, even when multiple sources emit at substantially the same time. Thus, electromagnetic radiation emitted from a first of the emitters 14 from a first perspective will be retro-reflected back toward the first of the emitters 14 by the markers 24, while electromagnetic radiation emitted from a second of the emitters 14 at a second perspective will be retro-reflected back toward the second of the emitters 14 by the markers 24, which enables multiple sets of tracking information to be produced and monitored by the control unit 18.

It is also now recognized that the retro-reflective markers 24 on the wall 93 and the floor 92 may be the same, or different. Indeed, the tracking system 10 may be configured to determine which electromagnetic radiation was reflected from the wall 93 versus which electromagnetic radiation was reflected from the floor 92 using a directionality of the retro-reflected electromagnetic radiation from the wall 93 and the floor 92. In other embodiments, different materials may be used for the markers 24 so that, for example, different wavelengths of electromagnetic radiation may be reflected back toward the emitter 14 and detector 16 by the different materials. As an example, the retro-reflective markers 24 on the floor 92 and the wall 93 may have the same retro-reflective elements, but different layers that act to filter or otherwise absorb portions of the emitted electromagnetic radiation so that electromagnetic radiation reflected by the retro-reflective markers 24 on the floor 92 and wall 93 have characteristic and different wavelengths. Because the different wavelengths would be retro-reflected, the detector 16 may detect these wavelengths and separate them from ambient electromagnetic radiation, which is filtered by filter elements within the detector 16.

Figure 8:
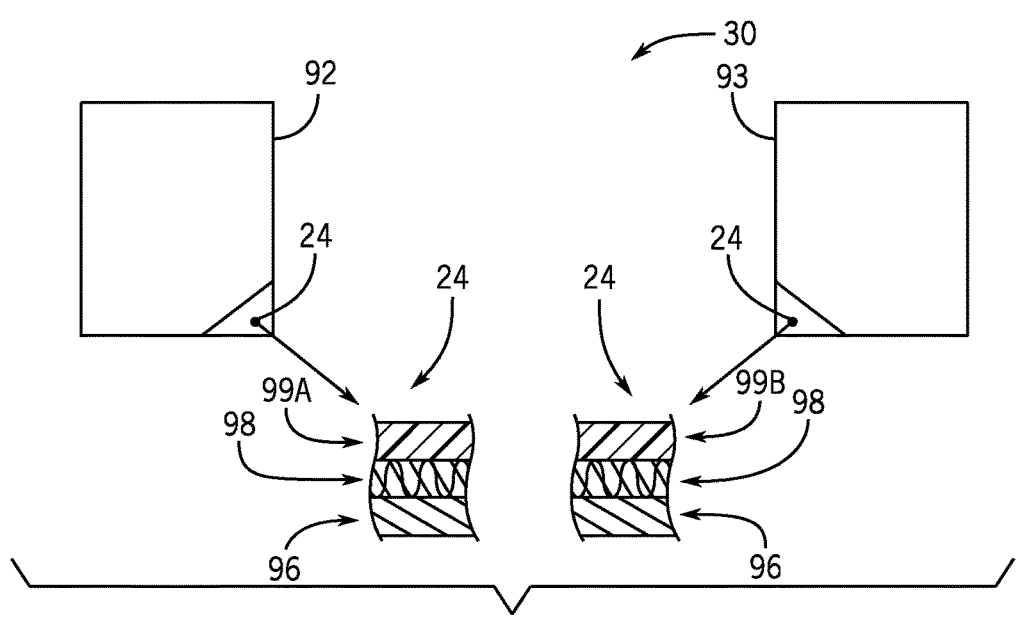
FIG. 8 illustrates cross-sections of retro-reflective markers having different coatings to enable different wavelengths of electromagnetic radiation to be reflected back toward the detector of the tracking system of FIG. 1, in accordance with an embodiment of the present disclosure.

To help illustrate, FIG. 8 depicts expanded cross-sectional views of example retro-reflective markers 24 disposed on the floor 92 and the wall 93 within the detection area 30. The markers 24 on the floor 92 and the wall 93 each include a reflective layer 96 and a retro-reflective material layer 98, which may be the same or different for the floor 92 and wall 93. In the illustrated embodiment, they are the same. During operation, electromagnetic radiation emitted by the emitter 14 may traverse a transmissive coating 99 before striking the retro-reflective material layer 98. Accordingly, the transmissive coating 99 may be used to adjust the wavelengths of electromagnetic radiation that are retro-reflected by the markers. In FIG. 8, the markers 24 on the floor 92 include a first transmissive coating 99A, which is different than a second transmissive coating 99B in the markers 24 on the wall 93. In certain embodiments, different optical properties between the first and second transmissive coatings 99A, 99B may cause a different bandwidth of electromagnetic radiation to be reflected by the markers 24 on the floor 92 and the markers 24 on the wall 93. While presented in the context of being disposed on the floor 92 and the wall 93, it should be noted that markers 24 having different optical properties may be used on a variety of different elements within the amusement park, such as on people and environmental elements, people and moving equipment, and so on, to facilitate separation for processing and monitoring by the control unit 18.

Any one or a combination of the techniques set forth above may be used to monitor a single object or person, or multiple objects or people. Indeed, it is presently recognized that a combination of multiple retro-reflective marker grids (e.g., on the floor 92 and wall 93 as set forth above), or a combination of one or more retro-reflective marker grids and one or more tracked retro-reflective markers 24 fixed on a movable object or person, may be utilized to enable three-dimensional tracking, even when only one detector 16 is utilized. Further, it is also recognized that using multiple retro-reflective markers 24 on the same person or object may enable the tracking system 10 to track both position and orientation.

In this regard, FIG. 9A illustrates an embodiment of the object 26 having multiple retro-reflective markers 24 positioned on different faces of the object 26. Specifically, in the illustrated embodiment, the retro-reflective markers 24 are disposed on three different points of the object 26 corresponding to three orthogonal directions (e.g., X, Y, and Z axes) of the object 26. However, it should be noted that other placements of the multiple retro-reflective markers 24 may be used in other embodiments. In addition, the tracking depicted in FIG. 9A may be performed as generally illustrated, or may also utilize a grid of the retro-reflective markers 24 as shown in FIG. 7.

As noted above, the tracking system 10 may include multiple detectors 16 configured to sense the electromagnetic radiation that is reflected back from the object 26, for example. Each of the retro-reflective markers 24 disposed on the object 26 may retro-reflect the emitted electromagnetic radiation beam 28 at a particular, predetermined frequency of the electromagnetic spectrum of the electromagnetic radiation beam 28. That is, the retro-reflective markers 24 may retro-reflect the same or different portions of the electromagnetic spectrum, as generally set forth above with respect to FIG. 8.

The control unit 18 is configured to detect and distinguish the electromagnetic radiation reflected at these particular frequencies and, thus, to track the motion of each of the separate retro-reflective markers 24. Specifically, the control unit 18 may analyze the detected locations of the separate retro-reflective markers 24 to track the roll (e.g., rotation about the Y axis), pitch (e.g., rotation about the X axis), and yaw (e.g., rotation about the Z axis) of the object 26. That is, instead of only determining the location of the object 26 in space relative to a particular coordinate system (e.g., defined by the detection area 30 or the detector 16), the control unit 18 may determine the orientation of the object 26 within the coordinate system, which enables the control unit 18 to perform enhanced tracking and analyses of the movement of the object 26 in space and time through the detection area 30. For instance, the control unit 18 may perform predictive analyses to estimate a future position of the object 26 within the detection area 30, which may enable enhanced control over the movement of the object 26 (e.g., to avoid collisions, to take a particular path through an area).

In certain embodiments, such as when the object 26 is a motorized object, the tracking system 10 may track the position and orientation of the object 26 (e.g., a ride vehicle, an automaton, an unmanned aerial vehicle) and control the object 26 to proceed along a path in a predetermined manner. The control unit 18 may, additionally or alternatively, compare the results to an expected position and orientation of the object 26, for example to determine whether the object 26 should be controlled to adjust its operation, and/or to determine whether the object 26 is operating properly or is in need of some sort of maintenance. In addition, the estimated position and orientation of the object 26, as determined via the tracking system 10, may be used to trigger actions (including preventing certain actions) by other amusement park equipment 12 (e.g., show effects). As one example, the object 26 may be a ride vehicle and the amusement park equipment 12 may be a show effect. In this example, it may be desirable to only trigger the amusement park equipment 12 when the object 26 is in the expected position and/or orientation.

Continuing with the manner in which tracking in three spatial dimensions may be preformed, FIG. 9B depicts an example of the object having a first marker 24A, a second marker 24B, and a third marker 24C positioned in similar positions as set forth in FIG. 9A. However, from the perspective of a single one of the detectors 16, the detector 16 may see a two-dimensional representation of the object 16, and the markers 24A, 24B, 24C. From this first perspective (e.g., overhead or bottom view), the control unit 18 may determine that the first and second markers 24A, 24B are separated by a first observed distance d1, the first and third markers 24A, 24C are separated by a second observed distance d2, and the second and third markers 24B, 24C are separated by a third observed distance d3. The control unit 18 may compare these distances to known or calibrated values to estimate an orientation of the object 26 in three spatial dimensions.

Moving to FIG. 9C, as the object 26 rotates, the detector 16 (and, correspondingly, the control unit 18) may detect that the apparent shape of the object 26 is different. However, the control unit 18 may also determine that the first and second markers 24A, 24B are separated by an adjusted first observed distance d1', the first and third markers 24A, 24C are separated by an adjusted second observed distance d2', and the second and third markers 24B, 24C are separated by an adjusted third observed distance d3'. The control unit 18 may determine a difference between the distances detected in the orientation in FIG. 9B and the distances detected in the orientation in FIG. 9C to determine how the orientation of the object 26 has changed to then determine the orientation of the object 26. Additionally or alternatively, the control unit 18 may compare the adjusted observed distances d1', d2', d3' resulting from rotation of the object 26 to stored values to estimate an orientation of the object 26 in three spatial dimensions, or to further refine an update to the orientation determined based on the change between the distances in FIGS. 9B and 9C.

As set forth above, present embodiments are directed to, among other things, the use of the disclosed tracking system 10 to track objects and/or people within an amusement park environment. As a result of this tracking, the control unit 18 may, in some embodiments, cause certain automated functions to be performed within various subsystems of the amusement park. Accordingly, having described the general operation of the disclosed tracking system 10, more specific embodiments of tracking and control operations are provided below to facilitate a better understanding of certain aspects of the present disclosure.

Figure 10:
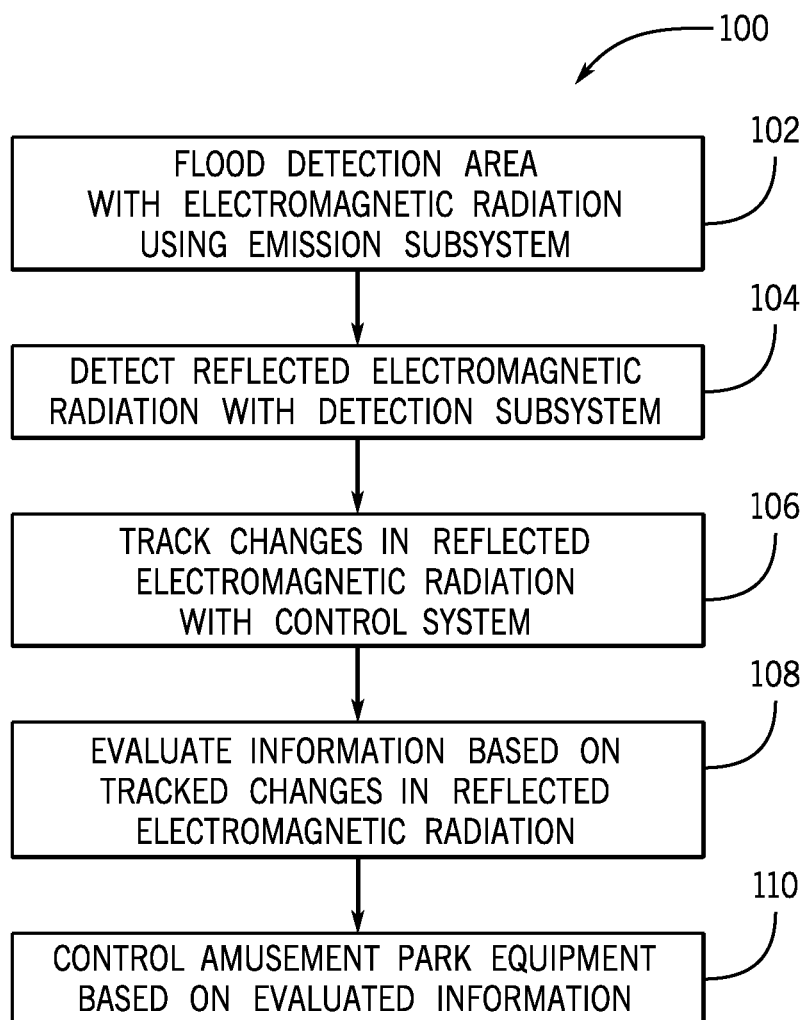
FIG. 10 is a flow diagram illustrating an embodiment of a method of tracking reflection and controlling amusement park elements based on the tracked reflection using the tracking system of FIG. 1, in accordance with an embodiment of the present disclosure.

Moving now to FIG. 10, an embodiment of a method 100 of monitoring changes in reflected electromagnetic radiation to track movement of a target and control amusement park equipment as result of this monitoring is illustrated as a flow diagram. Specifically, the method 100 includes the use of one or more of the emitters 14 (e.g., an emission subsystem) to flood (block 102) the detection area 30 with electromagnetic radiation (e.g., electromagnetic radiation beam 28) using the emission subsystem. For instance, the control unit 18 may cause one or more of the emitters 14 to intermittently or substantially continuously flood the detection area 30 with emitted electromagnetic radiation. Again, the electromagnetic radiation may be any appropriate wavelength that is able to be retro-reflected by the retro-reflective markers 24. This includes, but is not limited to, ultraviolet, infrared, and visible wavelengths of the electromagnetic spectrum. It will be appreciated that different emitters 14, and in some embodiments, different markers 24, may utilize different wavelengths of electromagnetic radiation to facilitate differentiation of various elements within the area 30.

After flooding the detection area 30 with electromagnetic radiation in accordance with the acts generally represented by block 102, the method 100 proceeds to detecting (block 104) electromagnetic radiation that has been reflected from one or more elements in the detection area 30 (e.g., the retro-reflective markers 24). The detection may be performed by one or more of the detectors 16, which may be positioned relative to the emitter 14 as generally set forth above with respect to FIGS. 1 and 2. As described above and set forth in further detail below, the features that perform the detection may be any appropriate element capable of and specifically configured to capture retro-reflected electromagnetic radiation and cause the captured retro-reflective electromagnetic radiation to be correlated to a region of the detector 16 so that information transmitted from the detector 16 to the control unit 18 retains position information regarding which of the markers 24 reflected electromagnetic radiation to the detector 16. As one specific but non-limiting example, one or more of the detectors 16 (e.g., present as a detection subsystem) may include charge coupled devices within an optical camera or similar feature.

As described above, during the course of operation of the tracking system 10, and while people 70 and/or objects 26, 32 are present within the detection area 30, it may be expected that changes in reflected electromagnetic radiation will occur. These changes may be tracked (block 106) using a combination of the one or more detectors 16 and routines performed by processing circuitry of the control unit 18. As one example, tracking changes in the reflected electromagnetic radiation in accordance with the acts generally represented by block 106 may include monitoring changes in reflected patterns from a grid over a certain period of time, monitoring changes in spectral signatures potentially caused by certain absorptive and/or diffusively or specularly reflective elements present within the detection area 30, or by monitoring certain moving retro-reflective elements. As described below, the control unit 18 may be configured to perform certain types of tracking of the changes in reflection depending on the nature of the control to be performed in a particular amusement park attraction environment.

At substantially the same time or shortly after tracking the changes in reflected electromagnetic radiation in accordance with the acts generally represented by block 106, certain information may be evaluated (block 108) as a result of these changes by the control unit 18. In accordance with one aspect of the present disclosure, the evaluated information may include information pertaining to one or more individuals (e.g., amusement park guests, amusement park employees) to enable the control unit 18 to monitor movement and positioning of various individuals, and/or make determinations relating to whether the person is appropriately positioned relative to certain amusement park features. In accordance with another aspect of the present disclosure, the information evaluated by the control unit 18 may include information relating to objects 26, 32, which may be environmental objects, moving objects, the amusement park equipment 12, or any other device, item, or other feature present within the detection area 30. Further details regarding the manner in which information may be evaluated is described in further detail below with reference to specific examples of amusement park equipment controlled at least in part by the control unit 18.

As illustrated, the method 100 also includes controlling (block 110) amusement park equipment based on the information (e.g., monitored and analyzed movement of people and/or objects) evaluated in accordance with acts generally represented by block 108. It should be noted that this control may be performed in conjunction with concurrent tracking and evaluation to enable the control unit 18 to perform many of the steps set forth in method 100 on a substantially continuous basis and in real-time (e.g., on the order of the rate of capture of the detector 16), as appropriate. In addition, the amusement park equipment controlled in accordance with the acts generally represented by block 110 may include automated equipment such as ride vehicles, access gates, point-of-sale kiosks, informational displays, or any other actuatable amusement park device. As another example, the control unit 18 may control certain show effects such as the ignition of a flame or a firework as a result of the tracking and evaluation performed in accordance with method 100. More details relating to certain of these specific examples are described in further detail below.

In accordance with a more particular aspect of the present disclosure, the present embodiments relate to the tracking of retro-reflective markers positioned on certain environmental and functional features of an amusement park attraction area using survey equipment. For example, in certain embodiments, park equipment may be monitored for degradation due to mechanical and/or environmental stresses. Using this information, the control unit 18 may provide information relating to the current state of the particular equipment and, in some embodiments, may provide recommendations for maintenance or other procedures. More specifically, the amusement park equipment 12 may include various systems configured to provide such information to ride operators, facilities engineers, and so forth. For example, the amusement park equipment 12 that may be controlled in relation to surveying certain amusement park features may include displays, report-generating features, and the like.

Figure 11:
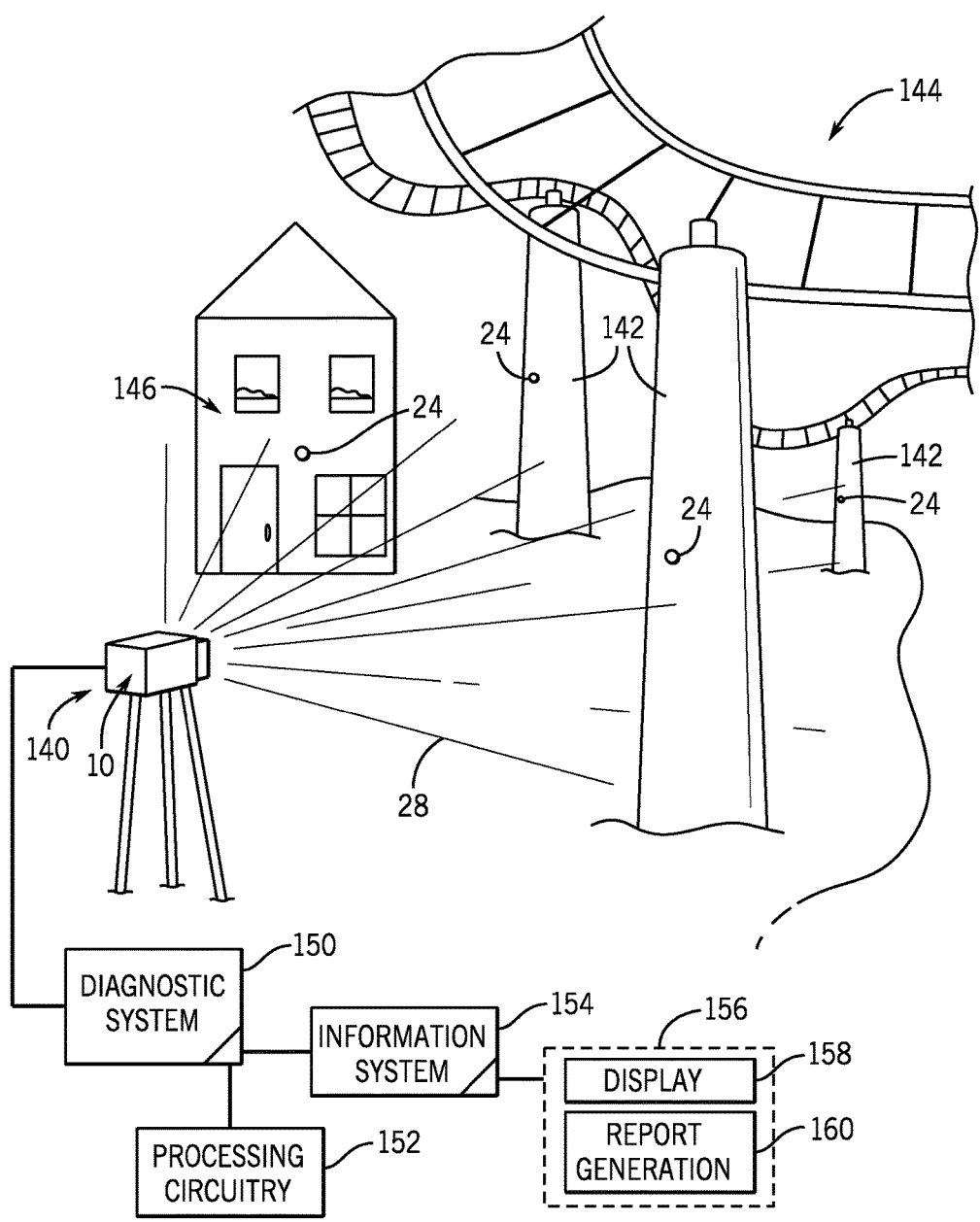
FIG. 11 is a perspective view of the tracking system of FIG. 1 being used in surveying equipment to determine changes in elevation or coloration of structures, in accordance with an embodiment of the present disclosure.

In the specific context of an amusement park, the tracking system 10 may be disposed in surveying equipment 140, as illustrated in FIG. 11, to determine a variety of maintenance-related information relating to roller coasters or similar rides, and/or relating to facilities housing certain amusement attraction features. In the illustrated embodiment, the surveying equipment 140 outputs the electromagnetic radiation beam 28 with a relatively large range to capture data representative of several different components in its field of view at the same time. These components may include, for example, supports 142 (e.g., ride column) of a roller coaster 144, building structures 146, and any other structures that may be in the field of view of the tracking system 10 within the surveying equipment 140. Any number of these components may be equipped with one or more of the retro-reflective markers 24.

In the illustrated embodiment, certain of the retro-reflective markers 24 are disposed on each of the supports 142 and the building structure 146. The surveying equipment 140 may survey this series of retro-reflective markers 24 nearly instantaneously, since they are all within the field of view of the tracking system 10. As described in further detail below, by evaluating the detected locations (both individual and in reference to each other) of the retro-reflective markers 24, it may be possible to determine whether settlement of any of these supports 142 or the building structure 146 has occurred over time. In addition, since the surveying equipment 140 can take readings of multiple such retro-reflective markers 24 at the same time via the tracking system 10, this may reduce the amount of time it takes to survey the area.

In accordance with a further embodiment, the tracking system 10 in the surveying equipment 140 may be used to determine whether a spectral shift has occurred over time on building structures 146 or other structures that have been painted. Specifically, the surveying equipment 140 may be used early on, when the building structure 146 has just been painted, to determine an amount of electromagnetic radiation reflected from the newly painted building structure 146. At a later point in time, the surveying equipment 140 may be used to detect the electromagnetic radiation reflected from the building structure 146, compare this reflected signature to the previously stored data, and determine whether spectral shift (e.g., paint fading) has occurred and if the building structure 146 should be repainted.

As also illustrated, the surveying equipment 140, and specifically the tracking system 10, may, in certain embodiments, be in communication with a diagnostic system 150. In still further embodiments, the diagnostic system 150 may be integrated as a part of the surveying equipment 140 and/or implanted within the tracking system 10 (e.g., as a part of the control unit 18). As one example, the tracking system 10 may obtain tracking data relating to the retro-reflective markers 24 and/or other optically detectable features of the building 146 and/or ride 144. The tracking system 10 may provide this information to the diagnostic system 150, which may include processing circuitry 152 such as one or more processors configured to execute diagnostic routines stored on a memory of the system 150. The memory may also include legacy information relating to prior analyses performed on the building 146 and ride 144, so that the state of these features may be tracked and compared over time.

The diagnostic system 150 may also include an information system 154 in communication with the surveying equipment 140 and the processing circuitry 152. The information system 154 may include various user interface features 156, such as one or more displays 158 and/or one or more report generation features 160. The user interface features 156 may be configured to provide users (e.g., operators, facilities engineers) with perceivable indicators relating to the evaluated health of the surveyed features and/or to provide the monitored data to the users to enable the users to analyze the data directly. However, it is within the scope of the present disclosure for the tracking system 10, the surveying equipment 140, and/or the diagnostic system 150 to analyze and interpret the monitored data to provide an indication to the users relating to whether the tracked amusement park feature is in need of maintenance.

Figure 12:
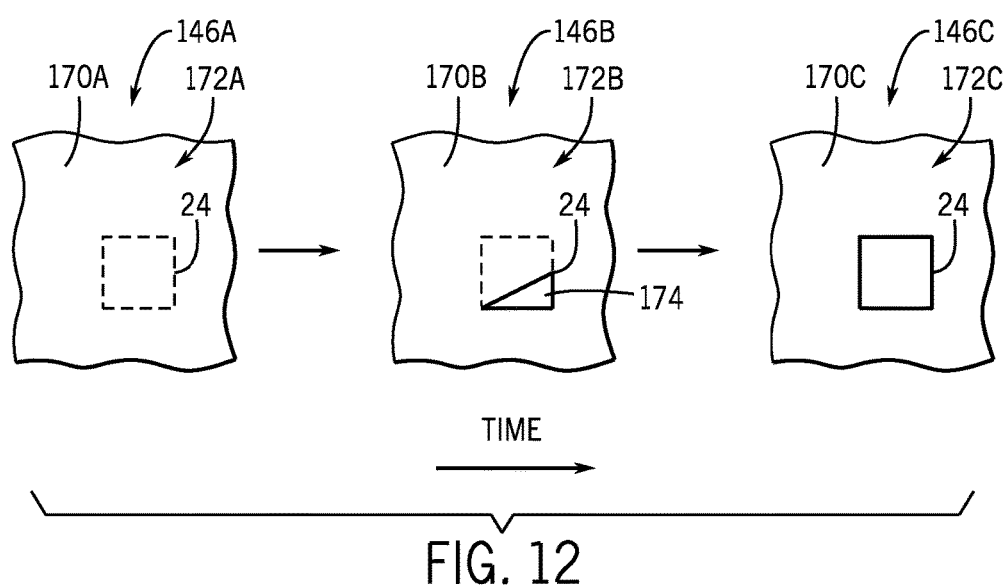
FIG. 12 is a schematic representation of the manner in which the tracking system of FIG. 1 monitors the change in a surface condition of a structure having a retro-reflective marker positioned under the surface, in accordance with an embodiment of the present disclosure.

Another example of the manner in which the surveying system 140 may be utilized in the context of evaluating a paint color and/or surface integrity of the building 146 is depicted in FIG. 12. Specifically, FIG. 12 depicts a portion 170 of the building 146 at different time points. The different time points of the building 146 may be considered to represent, by way of example, the effect of time as well as environmental stresses on the building 146. FIG. 12, as illustrated, includes the portion 170 at a first time point of the building 146, which is represented as 146A.

As shown at the first time point of the building 146A, the portion 170 includes one of the retro-reflective markers 24 disposed underneath a surface treatment 172. At the first time point, these are represented as portion 170A and surface treatment 172A. The surface treatment 172 may include, by way of example, a coating (e.g., paint) or a covering (e.g., brick, stucco). As shown, over time and upon exposure to various environmental stresses (e.g., weather, sunlight), the first surface treatment 172A begins to fade, thin, crack, peel, or otherwise degrade to a second surface treatment 172B (a degraded version of the first surface treatment 172A), which results in a portion 174 of the retro-reflective marker 24 being exposed.

The surveying equipment 140, and specifically the tracking system 10, may recognize this change by determining that the retro-reflective marker 24 is able to receive and retro-reflect the electromagnetic radiation emitted by the emitter 14 of the tracking system 10. The diagnostic system 150 may be configured to determine the degree to which the retro-reflective marker 24 has become exposed by, for example, tracking the intensity of the retro-reflected electromagnetic radiation and comparing the intensity to a stored intensity, pattern, etc. The diagnostic system 150 may also use the degree to which the retro-reflective marker 24 has become exposed to evaluate a relative degree of degradation of the surface treatment 172.

As also illustrated, the portion 170 may also progress to a third portion 170C having a third surface treatment 172C (a further degraded version of the second surface treatment 172B), where the retro-reflective marker 24 has become fully exposed. In such a situation, the tracking system 10 may recognize that the retro-reflective marker 24 has become fully exposed and may cause the information system 160 to provide a user-perceivable indication that the surface treatment 170C may need to be re-applied or otherwise repaired.

Figure 13:
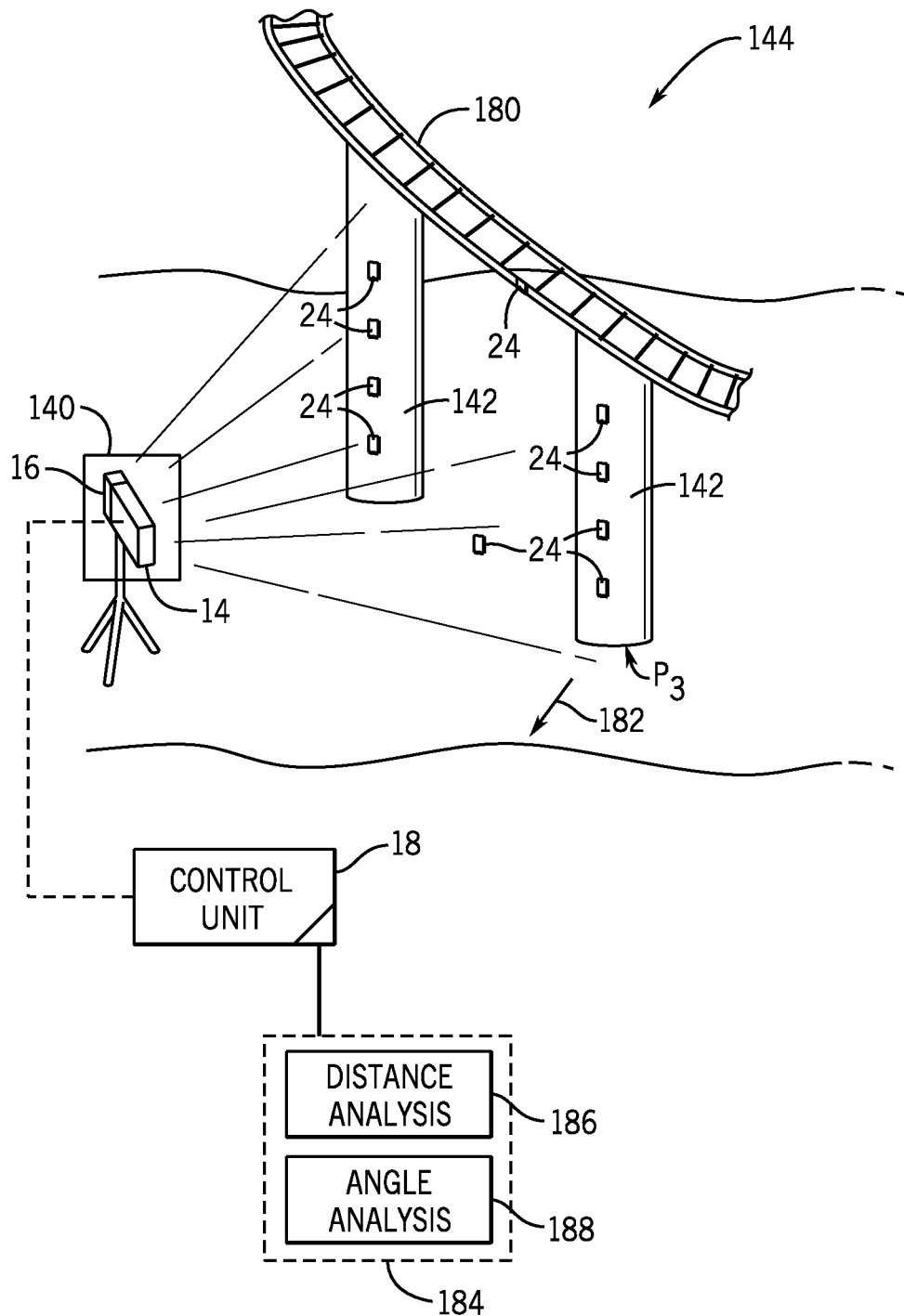
FIG. 13 is a perspective view of the tracking system of FIG. 1 being used to survey an amusement park ride, including support structures and a track, to determine changes in structural elevation of the ride, in accordance with an embodiment of the present disclosure.

In accordance with an aspect of the present disclosure, the surveying equipment 140 may, additionally or alternatively, be used to monitor a position of certain amusement park structural features, such as the supports 142 and/or a track 180 supported by the supports 142 as shown in FIG. 13. For example, over time, the supports 142 may settle into the ground 182, and it may be desirable to recognize and/or monitor this settling over time to determine whether maintenance may be required on the ride 144. Also, the track 180 on the supports 142 may also shift its position over time, for example by sagging or shifting horizontally due to gravity, use (e.g., vibrations), and other factors.

One or more of the retro-reflective markers 24 may be positioned on the supports 142, the track 180, and/or on the ground 182 (which may correspond to the floor 92 if the ride 144 is an indoor attraction). The retro-reflective markers 24 may be positioned on the supports 142 and the track 180 in regions where movement, degradation, sagging, settling, etc., is recognizable and/or most likely to occur. For example, as illustrated in FIG. 13, a plurality of retro-reflective markers 24 are positioned along a longitudinal axis of the supports 142, while one of the retro-reflective markers 24 is positioned on a portion of the track 180 between the supports 142, where settling or sagging might be most likely to occur.

The survey equipment 140 may, accordingly, identify a position of these markers 24 relative to a position of a certain environmental feature, such as the ground. The survey equipment 140 may include any number of features configured to perform surveying techniques and, indeed, the tracking system 10 of the present disclosure may simply be used in conjunction with such features, or in place of at least some of these features. By way of example, the survey equipment 140 may include any number of survey equipment features known in the art, such as a total station, a robotic total station, an electronic distance meter, a theodolite, or any combination of these or similar features. Furthermore, the control unit 18 may include or otherwise be in communication with various surveying circuitry 184, including (but not limited to) distance analysis circuitry 186 and/or angle analysis circuitry 188 compatible with, for example, distance meters and theodolites.

As one non-limiting example, all or a part of the tracking system 10, including the retro-reflective markers 24, may be used in combination with electronic distance measurement techniques to evaluate shifting of the different features of the ride 144. For instance, electronic distance measurement may generally be performed based on the emission of light, the detection of light reflected from a target, and the measurement of the phase difference between the emitted and reflected light. The phase difference can be used to determine the distance of the reflecting target from the emission source. Typically, one measurement would be performed at a time. However, in accordance with present embodiments, the detector 16 may be configured to capture multiple signals from multiple reflecting targets (i.e., multiple retro-reflective markers 24) without a loss of phase information. Accordingly, it is now recognized that the disclosed tracking system 10 may be integrated with existing surveying equipment and methodology to greatly enhance the speed by which survey measurement may be performed. It should be noted that equipment in accordance with present embodiments may also monitor vibration (e.g., slight shifts in equipment) during operation of the monitored system (e.g., a roller coaster). This may facilitate identification of components of the system (e.g., track segments) subject to increased wear.

As an example of the manner in which the tracking system 10 may be integrated with electronic distance measurement survey equipment to monitor shifting or excessive vibration of the ride 144, the emitter 14 may emit the electromagnetic radiation beam 28 into the detection area 30 including the supports 142 and track 180. The emission may be modulated using, for example, a quartz crystal oscillator that acts as an electronic shutter. The phase of the emitted electromagnetic radiation is, therefore, established by the system in accordance with present techniques.

The detector 16 may then capture and record the retro-reflected electromagnetic radiation from the retro-reflective markers 24 at substantially the same time. That is, the detector 16 may record both the source and the phase of the retro-reflected electromagnetic radiation from all of the retro-reflective markers 24 at once. This information may be provided to the surveying circuitry 184, which may compare the measured phase to the known phase of the emitted radiation. The distance to the retro-reflective markers 24 may then be calculated based, at least in part, on the difference in phase between the transmitted and the received electromagnetic radiation.

The calculated distances for the retro-reflective markers on the supports 142 may be compared to the markers 24 on the track 180 to identify, for instance, movement of the track 180 relative to the supports 142 (assuming that the markers 24 were positioned for a prior measurement for comparative or baseline purposes, and the markers 24 are in the same position). Settling of the supports 142 may be identified, for instance, based on changing distances between the ground (on which a reflector may be positioned, as shown), and the measured retro-reflective markers 24 on the supports 142. The supports 142 may also be measured relative to one another to identify whether one of the supports 142 might have moved relative to another, which could affect the track 180. As set forth above with respect to FIG. 11, the information obtained from these types of surveys may be relayed to the information system 154 to enable a technician to address any potential issues with the surveyed equipment.

Figure 14:
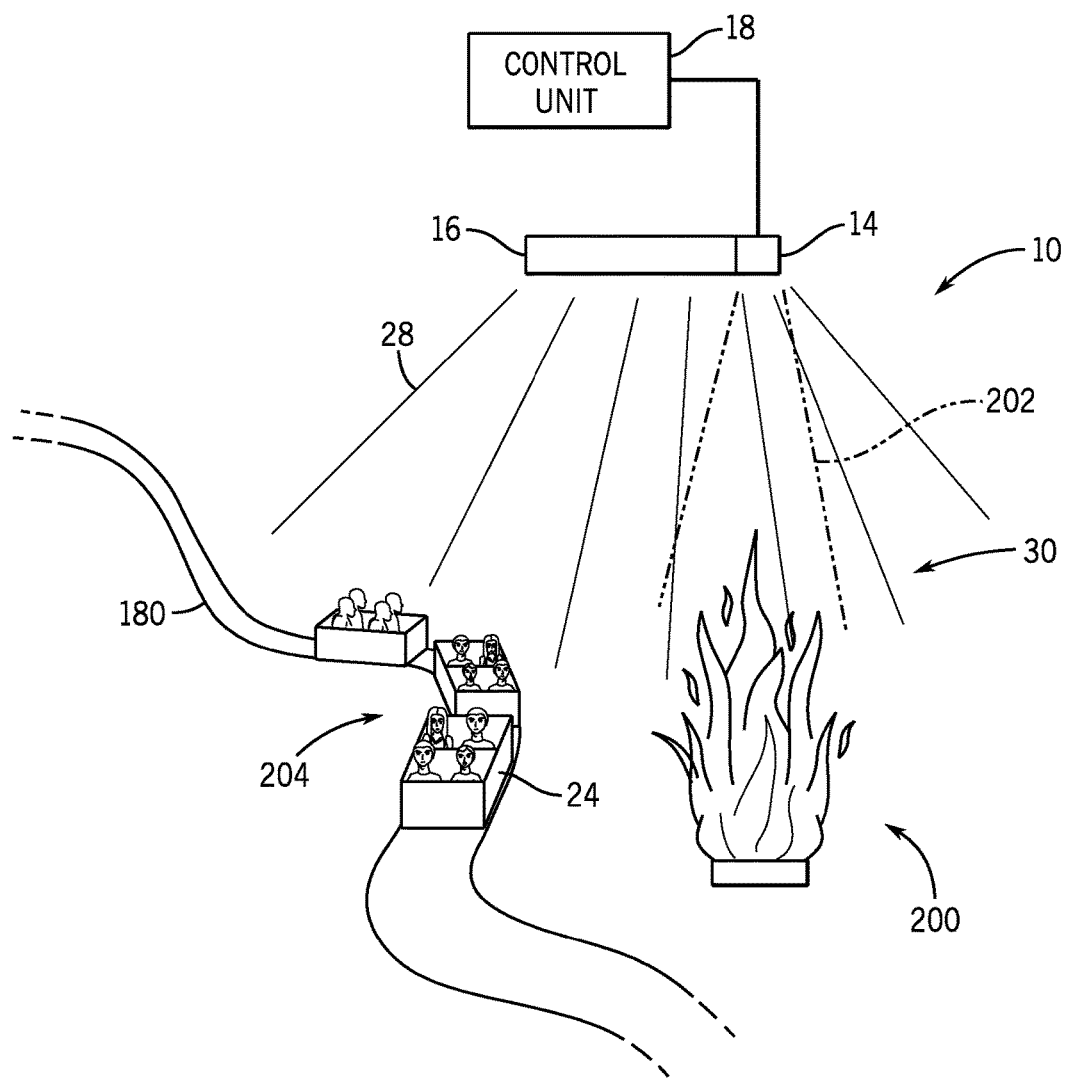
FIG. 14 is a perspective view of the tracking system of FIG. 1 used to monitor an amusement park ride vehicle and a flame effect, in accordance with an embodiment of the present disclosure.

In addition to or as an alternative to monitoring the structural health of various amusement park equipment, the presently disclosed tracking system 10 may also be used to track pyrotechnic show effects produced by various equipment and, if appropriate, adjust the equipment producing the pyrotechnic show effects. Such tracking and control may be applied, for example, to the production of a flame effect, to a firework show, or other setting. FIG. 14 illustrates an example of how the tracking system 10 may be used to identify and/or monitor a flame effect 200 (or some other heating effect). The flame effect 200 may be a part of an amusement park attraction such as a ride, a stunt show, or any other application where it is desirable to regularly provide a controlled flame. The flame effect 200 may, in certain embodiments, correspond to the production of a pattern of burning material, such as in a firework.

As discussed above with reference to FIG. 1, the control unit 18 of the tracking system 10 may be able to identify an object in the detection area 30 of the tracking system 10, without the use of the retro-reflective markers 24. That is, the control unit 18 may receive data indicative of the electromagnetic radiation reflected back from the detection area 30, and the control unit 18 may compare the signature of the reflected radiation to one or more possible data signatures stored in memory 22. In some embodiments, the control unit 18 may include a thermal signature stored in the memory 22, this thermal signature corresponding to the light from the flame effect 200 that is expected to reach the detector 16 when the flame effect 200 is operating properly. This thermal signature may be generated and stored in the memory 22 by repeatedly testing the flame effect 200 and averaging the electromagnetic radiation detected via the detector 16 over those multiple tests. Then, when the ride is operating, the control unit 18 may compare a thermal signature of detected electromagnetic radiation 202 from the flame effect 200 with the thermal signature stored in the memory 22.

The control unit 18 may trigger one or more pyrotechnic show effects based on a comparison made between the actual thermal signature detected via the detector 16 and the expected thermal signature. Specifically, if the thermal signature detected via the detector 16 is not approximately the same (e.g., within certain constraints) as the expected flame effect stored in the memory 22, the control unit 18 may signal the amusement park equipment 12 to notify a ride operator that the flame effect 200 is not functioning correctly, to actuate a sprinkler system within the ride area, to shut down the ride, and/or to stop the flame effect 200 altogether. Depending on whether the detected thermal signature is much larger or smaller than the desired thermal signature, one or more of these effects may be triggered via the control unit 18.

It should be noted that the same tracking system 10 (e.g., emitter 14 and detector 16) may simultaneously monitor both the flame effect 200 and other portions of the ride. For example, in the illustrated embodiment, the tracking system 10 is positioned to detect both the thermal signature of electromagnetic radiation from the flame effect 200 and a position of a ride vehicle 204 moving along the track 180. To that end, the ride vehicle 204 may include one or more retro-reflective markers 24 disposed thereon for tracking the motion of the ride vehicle 204 via the same tracking system 10 that monitors the flame effect 200, as long as the frequency of light reflected by the retro-reflective marker 24 is distinguishable from the flame effect signature. Due to the tracking system's ability to detect the retro-reflective marker 24 even in the presence of electromagnetic radiation including the wavelengths emitted by the emitter 14, the electromagnetic radiation from the flame effect 200 does not prevent the control unit 18 from identifying and locating the retro-reflective marker 24 on the ride vehicle 204. Thus, one tracking system 10 may be used to accomplish what would traditionally be accomplished using two or more distinct and functionally different detection systems, one for the flame effect 200 and another for the ride vehicle 204. Similar techniques may be applied in other contexts where it is desirable to detect a location of one object located near a flame effect (or some other bright effect) (e.g., an ordinance during a firework display).

Figure 15:
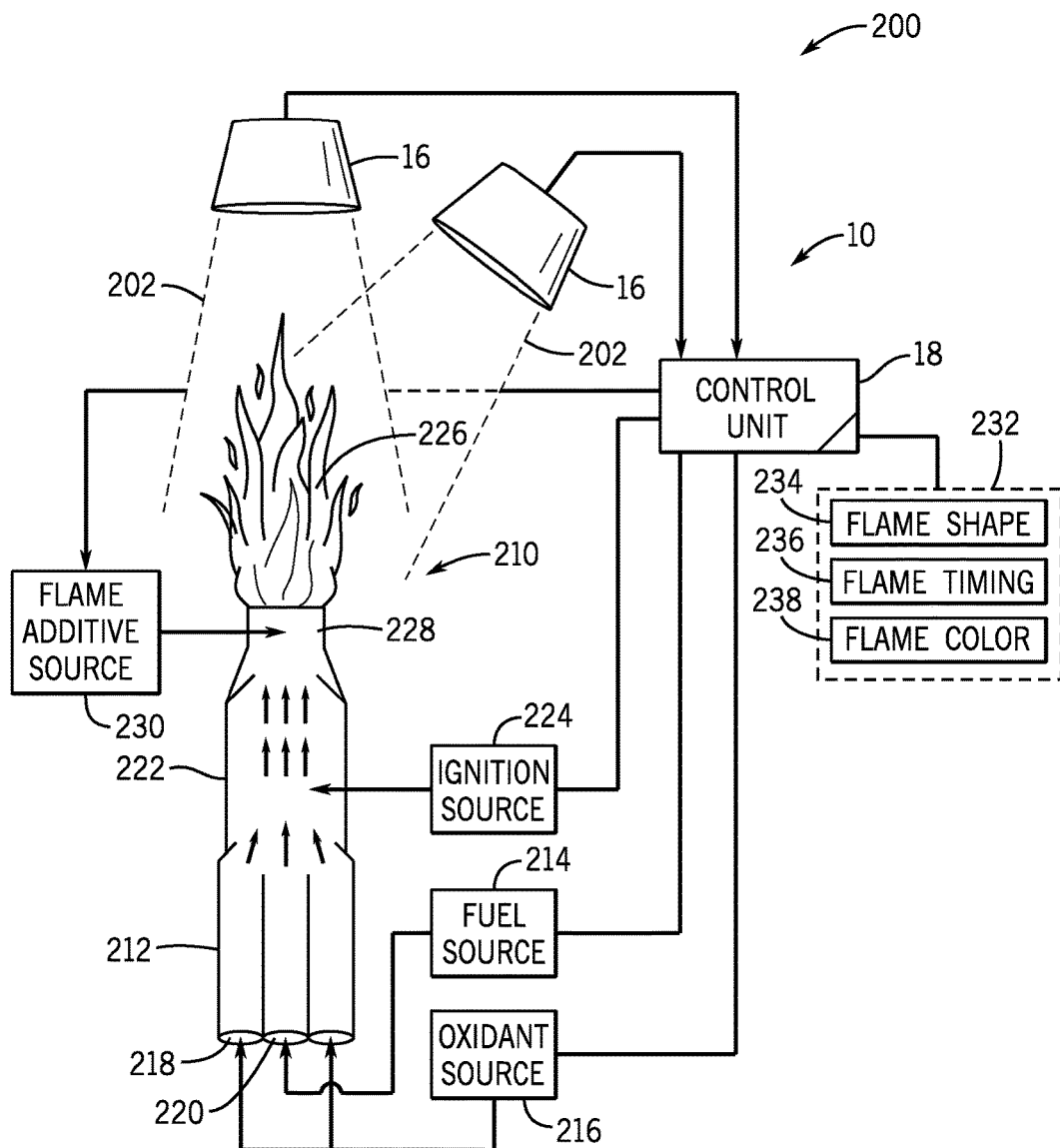
FIG. 15 is a cross-sectional side view of a flame-producing device monitored and controlled by the tracking system of FIG. 1, in accordance with an embodiment of the present disclosure.

FIG. 15 illustrates an embodiment of the flame effect 200 and the manner in which the tracking system 10 may be used to control and adjust the operation of the flame effect 200. Specifically, the flame effect 200 includes a flame-producing device 210, which includes a nozzle 212 configured to mix a fuel provided from a fuel source 214 and an oxidant provided from an oxidant source 216. The nozzle 212 may have a respective fuel inlet 218 and a respective oxidant inlet 220 configured to receive the fuel and the oxidant into the nozzle 212. These may constitute the inlets of the flame-producing device 210, or may be separate from the inlets thereof.

The flame-producing device 210 also includes a combustion chamber 222, where the mixed fuel and oxidant are ignited using an ignition source 224 (e.g., one or more spark plugs). The combustion produces a flame 226, which protrudes from an outlet 228 of the flame-producing device 210. One or more flame additives from a flame additive source 230 may be added to the flame 226 to adjust the color of the flame 226. For example, the flame additives may include metal salts, which may change the color of the flame 226 from orange and red to blue, green etc.

The control unit 18, using one or more of the detectors 16, may monitor the optical qualities of the flame 226 and, as a result of this monitoring, may perform certain control actions to adjust the flame 226 as appropriate. For example, the control unit 18 may be communicatively coupled to any one or a combination of the fuel source 214, oxidant source 216, ignition source 214, and flame additive source 230 to adjust the flame 226. As also illustrated, control unit 18 may include flame analysis circuitry 232, including flame shape analysis circuitry 234 configured to analyze a shape of the flame 226, flame timing analysis circuitry 236 configured to analyze a timing of the flame 226, and flame color analysis circuitry 238 configured to analyze the colors of the flame 226. The control unit 18, as an example, may control an amount of fuel and/or oxidant provided to the nozzle 212 by controlling the fuel and/or oxidant sources 214, 216. Similarly, the control unit 18 may control the timing of the flame 226 by adjusting the ignition source 224, and may adjust a color of the flame 226 by adjusting a flame additive provided by the flame additive source 230 (e.g., an amount of the additive) and/or the fuel source 214 (e.g., a flow of the fuel) and/or the oxidant source 216 (e.g., a flow of the oxidant).

Figure 16:
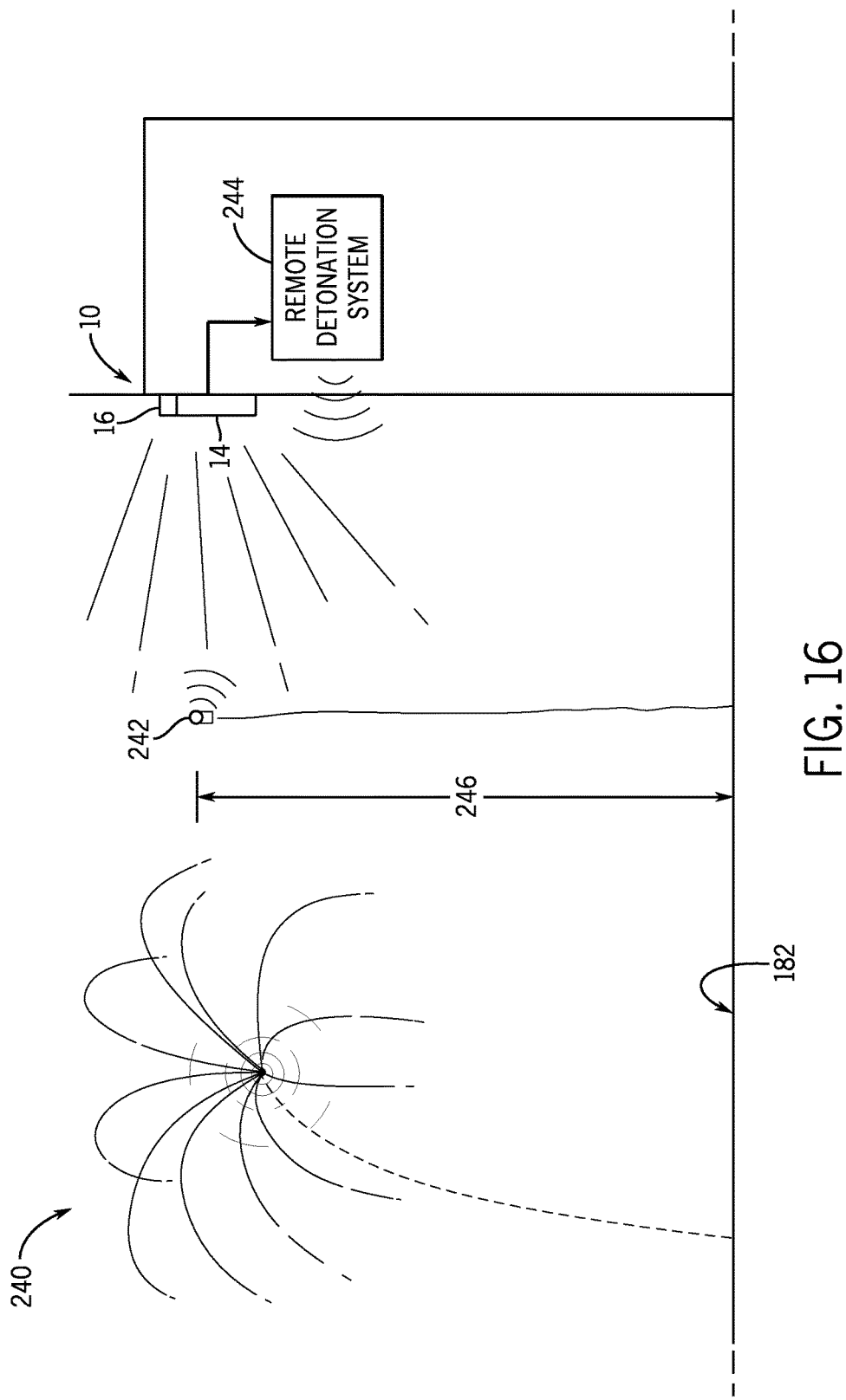
FIG. 16 is a perspective view of the tracking system of FIG. 1 being used to monitor a height of ordinances in a firework show, in accordance with an embodiment of the present disclosure.

Similar applications exist for equipment incorporating the tracking system 10 disclosed herein. For example, as illustrated in FIG. 16, the tracking system 10 may be used to control a firework (or ordinance) show 240 performed in a pyrotechnic show area, for example to enable enhanced monitoring and control of firework timing. Indeed, the tracking system 10 may use aspects relating to surveying (e.g., distance measurement) as well as flame monitoring in controlling the firework show 240. Since there may inherently be some variability between how long after a fuse is lit before the individual ordinance will ignite and explode as a firework, as well as how high the ordinance has traveled upward prior to ignition, it is now recognized that more accurate systems for controlling the height at which these ordinances reach before ignition is desired. This may produce a more consistent show.

In accordance with present embodiments, the tracking system 10 may be used to detect and track an ordinance 242 as it travels upward through the air. The tracking system 10 may send a signal indicative of the height of the ordinance above the ground 182 to a remote detonation system 244, which may communicate wirelessly with a detonator in the ordinance 242. When the ordinance 242 reaches a desirable height 246 above the ground, the remote detonation system 244 may send a wireless signal to the detonator in the ordinance 242 to initiate ignition and explosion of the ordinance 242 at approximately the desired height 246.

FIG. 17 illustrates an example embodiment of the ordinance 242 and the manner in which the tracking system 10 may track the ordinance 242 during flight. As illustrated in FIG. 17, the ordinance 242 includes an outer casing 260 enclosing various features of the ordinance 242. In certain embodiments, the internal features include a fuse 262 (which also extends out of the casing 260), which is lit and is used to ignite a lift charge 264. The lift charge 264 is typically responsible for the height that the ordinance 242 will reach in the air. However, as set forth below, the ordinance 242 may be launched using other features, such as compressed air. Accordingly, the ordinance 242 may not include the fuse 262. The presently disclosed ordinance 242 may include electronic detonator features (e.g., an electronic fuse mechanism), such as an electronic detonator 266 and a transceiver 268 configured to receive detonation signals from the remote detonation system 244. The ordinance 242 may include an internal fuse 270 connected to the electronic detonator 266, or a standalone fuse 271 coupled to the lift charge 264. The electronic detonator 266 may be configured to ignite a burst charge 272 via the internal fuse 270. However, other embodiments may utilize the standalone fuse 271 that is not coupled to an electronic feature for detonation. The burst charge 272 causes a plurality of pyrotechnic features (pyrotechnic show elements) commonly referred to as "stars" 274, to be released and burned. Typically, the stars 274 include a mixture of metal salts that, when burned, produce color.

As also illustrated, one or more of the retro-reflective markers 24 may be positioned on the outer casing 260. The marker 24 may enable the tracking system 10 to track the ordinance 242 after the lift charge 264 is ignited and while the ordinance 242 is in the air. For example, the emitter 14 and the detector 16 may be positioned on the building 146, and the detector 16 may track the marker 24 through the flight of the ordinance 242 to determine how high the ordinance 242 was before it burst. The triggering of the pyrotechnic show elements may be detected by the control unit 18, for example, by detecting a pattern of electromagnetic radiation associated with the pyrotechnic show elements (the stars 274) stored in the memory 22. The control unit 18 may be configured to determine a location at which the ordinance 242 detonated based on the detected triggering of the pyrotechnic show elements. Additionally or alternatively, the control unit 18 may track the movement of the ordinance 242 through the air (i.e., track its trajectory), and identify a triggering event of the ordinance 242 (detonation of the ordinance 242) when the retro-reflective marker 24 on the enclosure 260 is no longer visible to the detector 16 (e.g., termination of the retro-reflection by the retro-reflective marker 24 is associated with detonation of the ordinance 242).

Additionally or alternatively, the control unit 18, using routines stored in memory 22 and executed by processor 20, may track the ordinance 242 and relay instructions to the remote detonation system 244 to initiate detonation of the ordinance 242. Specifically, the remote detonation system 244 may include processing circuitry such as one or more processors 280 configured to, using instructions stored in one or more memory 282, interpret signals (e.g., data, instructions) from the control unit 18. As a result, the remote detonation system 244 may send wireless control signals from a transceiver 284 and to the respective transceiver 268 of the ordinance 242 to initiate detonation using the detonation electronics. As one example, the control unit 18 may provide either or both of height data and/or explicit detonation instructions.

The tracking system 10 may also be used to adjust ordinance trajectory, where appropriate. For example, as shown in FIG. 18, the tracking system 10 may track a plurality of the ordinances 242 as they travel through the air by tracking the retro-reflective markers 24 positioned on their casings 260 (see FIG. 17). The ordinances 242, in some embodiments, may be fired from cannons 290 mounted on robotic arms 292 attached to a base 294 on the ground 192. The robotic arms 292 may have articulation 296 along at least one axis, for example between one and six, to allow the ordinances 242 to be fired along any appropriate trajectories for the firework show 240.

In operation, the tracking system 10 may track the ordinances 242 and may also track their associated burst patterns 298 to determine launch trajectory and the location where the ordinances 242 ultimately detonated using, for example, firework trajectory control circuitry 300. In certain embodiments, the control unit 18 may have a predetermined firework show sequence stored in memory 22 (see FIG. 1), where the show sequence includes associated burst patterns, timing, trajectory, and so forth. The control unit 18 may perform substantially real-time comparisons between the tracked locations of the ordinances 242 and their burst patterns 298 to stored locations and associated burst patterns, and the timing associated with this stored information, and, using the trajectory control circuitry 300, cause actuation of the robotic arms 292 to adjust a position of the cannons 290. The adjustment may be performed so that the monitored trajectories of the ordinances 242 and locations of burst patterns 298 are appropriately correlated to the corresponding information stored in memory 22 associated with the stored firework show.

As noted above, in certain embodiments, the ordinance 242 may not include a lift charge. Instead, the ordinance 242 may be launched out of the cannons 290 using a compressed gas (e.g., compressed air) provided by a compressed gas source 302. In this regard, the amount of compressed gas (e.g., a pressure of the compressed gas) provided to the cannons 290 may determine, at least in part, a trajectory of the ordinance 242 through the air, how high the ordinance 242 is before it detonates, and so forth. As illustrated, the control unit 18 may be communicatively coupled to the compressed gas source 302, and may adjust the amount of compressed gas provided by the compressed gas source 302 to the cannons 290 to adjust a launch velocity of the ordinance 242 out of the cannons 290. For example, such adjustments may be provided based on comparisons between an expected (e.g., stored, reference) trajectory of the ordinance 242 and a measured trajectory of the ordinance 242. In this way, subsequent ordinances 242 having substantially the same configuration as the tracked ordinances 242 may have trajectories that are adjusted by the control unit 18 to more closely match the stored or reference trajectory.

While only certain features of the present embodiments have been illustrated and described herein, many modifications and changes will occur to those skilled in the art. It is, therefore, to be understood that the appended claims are intended to cover all such modifications and changes as fall within the true spirit of the invention.

The invention claimed is:

1. An amusement park surveying system, comprising:
    an amusement park feature having a retro-reflective marker;
    an emitter configured to emit electromagnetic radiation toward the retro-reflective marker;
    a detector configured to detect retro-reflection of the electromagnetic radiation from the retro-reflective marker while filtering electromagnetic radiation that is not retro-reflected; and
    a control system communicatively coupled to the detector and comprising processing circuitry configured to:
        monitor the retro-reflected electromagnetic radiation from the retro-reflective marker against a reference signature of retro-reflected electromagnetic radiation from the retro-reflective marker stored in memory; and
        identify differences between the electromagnetic radiation retro-reflected by the retro-reflective marker and the reference signature of retro-reflected electromagnetic radiation to evaluate a condition of the amusement park feature and to determine whether the amusement park feature is in need of maintenance.

2. The system of claim 1, comprising an informational system configured to provide a user-perceivable indication relating to the evaluation of the condition of the amusement park feature.

3. The system of claim 1, wherein the detector comprises one or more optical filters configured to filter out electromagnetic radiation that is not retro-reflected such that the detector maintains a signal to noise ratio above a threshold level even when electromagnetic radiation in the ambient environment comprises wavelengths that overlap with the electromagnetic radiation that is retro-reflected by the retro-reflective marker.

4. The system of claim 1, wherein the amusement park feature is a building having the retro-reflective marker positioned on an exterior of the building, and the retro-reflective marker is positioned underneath a surface treatment of the exterior.

5. The system of claim 4, wherein the reference signature of retro-reflected electromagnetic radiation from the retro-reflective marker stored in memory has a substantial lack of retro-reflected electromagnetic radiation by the retro-reflective marker due to total coverage of the retro-reflective marker by the surface treatment.

6. The system of claim 4, wherein the processing circuitry of the control system is configured to evaluate a degree of degradation of the surface treatment based on an amount of retro-reflected electromagnetic radiation from the retro-reflective marker.

7. The system of claim 6, wherein the processing circuitry of the control system is configured to cause an informational system in communication with the control system to produce a user-perceivable indication that the surface treatment needs maintenance.

8. The system of claim 1, wherein the amusement park feature comprises a support feature of an amusement park ride having the retro-reflective marker, and wherein the processing circuitry of the control system is configured to monitor retro-reflection of the electromagnetic radiation by the retro-reflective marker to evaluate movement of the retro-reflective marker, and correlate movement of the retro-reflective marker to movement of the support feature.

9. The system of claim 8, wherein the processing circuitry of the control system is configured to evaluate movement of the retro-reflective marker by identifying a degree of movement of the retro-reflective marker based on a change in a pattern of retro-reflected electromagnetic radiation by the retro-reflective marker, and comparing the degree of movement of the retro-reflective marker to a movement threshold.

10. The system of claim 1, comprising a stabilization support on which the emitter and detector are disposed, wherein the stabilization support is configured to establish a baseline orientation of the emitter and detector.

11. The system of claim 1, wherein the processing circuitry of the control system is configured to identify a degree of movement of the retro-reflective marker over time to evaluate whether the amusement park feature has settled over time.

12. The system of claim 1, wherein the amusement park feature comprises a ride system and wherein the processing circuitry of the control system is configured to identify a degree of movement of the retro-reflective marker during operation of the ride system to evaluate a degree of movement of the amusement park feature during operation of the ride system, and wherein the processing circuitry of the control system is configured to compare the evaluated degree of movement of the amusement park feature to a threshold degree of movement to make the determination of whether the amusement park feature is in need of maintenance.

13. The system of claim 1, wherein the emitter, the detector, and at least a portion of the processing circuitry of the control system are integrated with or form a part of surveying equipment, the surveying equipment comprising a total station, a robotic total station, an electronic distance meter, a theodolite, or any combination thereof.

14. The system of claim 13, comprising a plurality of retro-reflective markers positioned on a plurality of support features of an amusement park ride, wherein the surveying equipment comprises the electronic distance meter, and wherein processing circuitry of the control system is configured to determine a distance from the surveying equipment having the emitter and the detector to each support feature of the plurality of support features based on simultaneous detection of electromagnetic radiation retro-reflected from the plurality of retro-reflective markers.

15. The system of claim 14, wherein the processing circuitry of the control system is configured to evaluate movement of each support feature of the plurality of support features relative to at least one other support feature of the plurality of support features to determine whether the support feature has moved relative to the at least one other support feature of the plurality of support features.

16. A method of surveying amusement park features, comprising:
   directing electromagnetic radiation toward an amusement park feature positioned within an amusement park attraction area using an emitter, the amusement park feature having a retro-reflective marker;
   detecting electromagnetic radiation retro-reflected from the retro-reflective marker disposed on the amusement park feature while filtering out electromagnetic radiation that is not retro-reflected using a detector;
   monitoring the retro-reflected electromagnetic radiation from the retro-reflective marker against a reference signature of retro-reflected electromagnetic radiation from the retro-reflective marker stored in memory using processing circuitry of a control system in communication with the detector; and
   identifying differences between the electromagnetic radiation retro-reflected by the retro-reflective marker and the reference signature of retro-reflected electromagnetic radiation to evaluate a condition of the amusement park feature and to determine whether the amusement park feature is in need of maintenance.

17. The method of claim 16, wherein directing electromagnetic radiation toward the amusement park feature comprises directing the electromagnetic radiation toward a building having the retro-reflective marker positioned on an exterior of the building, and the retro-reflective marker is positioned underneath a surface treatment of the exterior, and wherein the method comprises evaluating, using the control system, a degree of degradation of the surface treatment based on an amount of retro-reflected electromagnetic radiation from the retro-reflective marker detected by the detector.

18. The method of claim 16, wherein directing electromagnetic radiation toward the amusement park feature comprises directing the electromagnetic radiation toward a support feature of an amusement park ride having the retro-reflective marker, and wherein the method comprises:
   monitoring retro-reflection of the electromagnetic radiation by the retro-reflective marker to evaluate movement of the retro-reflective marker using the control system based on position information associated with the retro-reflective marker; and
   correlating movement of the retro-reflective marker to movement of the support feature using the control system.

19. The method of claim 18, comprising:
comparing a degree of the movement of the support feature to a threshold degree of movement using the control system;
identifying whether the support feature is in need of maintenance based on the comparison between the degree of the movement of the support feature and the threshold degree of movement using the control system; and
generating a user-perceivable indication that the support feature is in need of maintenance if the degree of movement of the support feature is greater than the threshold degree of movement using the control system and an information system in communication with the control system.

20. A survey system configured to survey amusement park features, comprising:
   a retro-reflective marker;
   an emitter configured to emit electromagnetic radiation toward the retro-reflective marker;
   a detector correlated to electromagnetic radiation retro-reflected by the retro-reflective marker and configured to detect retro-reflection of the electromagnetic radiation from the retro-reflective marker while filtering electromagnetic radiation that is not retro-reflected; and
   a control system communicatively coupled to the emitter and the detector and comprising processing circuitry configured to:
      monitor the retro-reflected electromagnetic radiation from the retro-reflective marker against a reference signature of retro-reflected electromagnetic radiation from the retro-reflective marker stored in memory; and
      identify differences between the electromagnetic radiation retro-reflected by the retro-reflective marker and the reference signature of retro-reflected electromagnetic radiation, including differences in position or orientation, to evaluate a condition of an amusement park feature and to determine whether the amusement park feature is in need of maintenance; and
   wherein the emitter, the detector, and at least a portion of the processing circuitry of the control system are integrated with or form a part of surveying equipment, the surveying equipment comprising a total station, a robotic total station, an electronic distance meter, a theodolite, or any combination thereof.

* * * * *